US011553857B1

(12) United States Patent
Filipovic et al.

(10) Patent No.: US 11,553,857 B1
(45) Date of Patent: Jan. 17, 2023

(54) SYSTEM AND METHOD FOR THROUGH WINDOW PERSONAL CLOUD TRANSMISSION

(71) Applicant: Micro Mobio Corporation, Palo Alto, CA (US)

(72) Inventors: Zlatko Aurelio Filipovic, San Jose, CA (US); Weiping Wang, Palo Alto, CA (US); Adam James Wang, Palo Alto, CA (US); Guan-Wu Wang, Palo Alto, CA (US); Yi-Hung Chen, Hsinchu (TW)

(73) Assignee: Micro Mobio Corporation, Palo Alto, CA (US)

( * ) Notice: Subject to any disclaimer, the term of this patent is extended or adjusted under 35 U.S.C. 154(b) by 133 days.

(21) Appl. No.: 17/163,381

(22) Filed: Jan. 30, 2021

Related U.S. Application Data

(63) Continuation-in-part of application No. 16/595,914, filed on Oct. 8, 2019, now Pat. No. 11,058,326, which
(Continued)

(51) Int. Cl.
*H04W 4/90* (2018.01)
*A61B 5/11* (2006.01)
(Continued)

(52) U.S. Cl.
CPC .............. *A61B 5/1117* (2013.01); *A61B 3/14* (2013.01); *A61B 5/0022* (2013.01); *A61B 5/01* (2013.01); *A61B 5/02438* (2013.01); *A61B 5/1112* (2013.01); *A61B 5/332* (2021.01); *A61B 5/6831* (2013.01); *A61B 5/6898* (2013.01); *A61B 5/742* (2013.01); *A61B 5/748* (2013.01); *G06F 1/163* (2013.01); *G06F 1/1628* (2013.01); *G06F 1/1632* (2013.01); *G06F 1/1633* (2013.01); *G06F 1/1698* (2013.01); *G06F 1/183* (2013.01); *G06F 21/32* (2013.01); *G06F 21/70* (2013.01); *H04B 1/385* (2013.01); *H04B 1/3888* (2013.01); *H04M 1/0254* (2013.01); *H04W 4/90* (2018.02); *A61B 2560/0242* (2013.01);
(Continued)

(58) Field of Classification Search
CPC ........ H04W 4/90; A61B 5/742; A61B 5/1117; A61B 5/0022; A61B 5/02438
See application file for complete search history.

(56) References Cited

U.S. PATENT DOCUMENTS 3,671,379 A 6/1972 McCain
4,934,983 A 6/1990 Mayo
(Continued)

*Primary Examiner* — Congvan Tran
(74) *Attorney, Agent, or Firm* — Roark IP

(57) ABSTRACT

A radio frequency (RF) front end device has a signal traveling from a first antenna to a second antenna in an uplink path and a signal traveling from a third antenna to a fourth antenna in a downlink path. The device is under the control of automatic on/off controller (AOOC) which upon receiving a signal indication from a receive signal detector and amplifier (RSDA) turns on the operations of power amplifier (PA) and simultaneously turns off a low noise amplifier (LNA). This LNA is turned off when the power amplifier is turned on to prevent uplink path and downlink path forming a feedback loop which would result in oscillation, noise and interference.

15 Claims, 26 Drawing Sheets

Related U.S. Application Data is a continuation-in-part of application No. 15/614,555, filed on Jun. 5, 2017, now Pat. No. 10,437,295, which is a continuation-in-part of application No. 14/803,828, filed on Jul. 20, 2015, now Pat. No. 9,671,835, which is a continuation of application No. 13/831,663, filed on Mar. 15, 2013, now Pat. No. 9,086,847.

(60) Provisional application No. 62/968,147, filed on Jan. 30, 2020, provisional application No. 62/757,052, filed on Nov. 7, 2018, provisional application No. 61/705,383, filed on Sep. 25, 2012.

(51) Int. Cl.

| | | |
|---|---|---|
| *G06F 1/16* | (2006.01) | |
| *A61B 5/332* | (2021.01) | |
| *H04B 1/3888* | (2015.01) | |
| *H04M 1/02* | (2006.01) | |
| *G06F 1/18* | (2006.01) | |
| *G06F 21/32* | (2013.01) | |
| *G06F 21/70* | (2013.01) | |
| *A61B 3/14* | (2006.01) | |
| *A61B 5/01* | (2006.01) | |
| *A61B 5/00* | (2006.01) | |
| *A61B 5/024* | (2006.01) | |
| *H04B 1/3827* | (2015.01) | |
| *H04W 88/08* | (2009.01) | |
| *H04M 1/18* | (2006.01) | |
| *H04M 1/72409* | (2021.01) | |
| *H04M 1/72412* | (2021.01) | |
| *H04W 84/04* | (2009.01) | |
| *H04W 84/12* | (2009.01) | |
| *H04W 4/80* | (2018.01) | |

(52) U.S. Cl.
 CPC ............ *A61B 2560/0252* (2013.01); *A61B 2560/0257* (2013.01); *A61B 2562/0219* (2013.01); *H04M 1/185* (2013.01); *H04M 1/72409* (2021.01); *H04M 1/72412* (2021.01); *H04W 4/80* (2018.02); *H04W 84/04* (2013.01); *H04W 84/12* (2013.01); *H04W 88/08* (2013.01)

(56) References Cited

U.S. PATENT DOCUMENTS

| | | | |
|---|---|---|---|
| 5,161,255 A | 11/1992 | Tsuchiya | |
| 5,365,145 A | 11/1994 | Fields | |
| 5,678,228 A | 10/1997 | Soleimani | |
| 5,737,684 A | 4/1998 | Goto | |
| 6,049,315 A | 4/2000 | Meyer | |
| 6,081,232 A | 6/2000 | Pittman | |
| 6,442,018 B1 | 8/2002 | Dinkin | |
| 6,448,930 B1 | 9/2002 | Judd | |
| 6,603,754 B1 | 8/2003 | Park | |
| 6,661,386 B1 | 12/2003 | Petros | |
| 6,684,059 B1 | 1/2004 | Moerder | |
| 6,810,817 B1 | 11/2004 | James | |
| 7,020,890 B1 | 3/2006 | Suematsu | |
| 7,047,339 B2 | 5/2006 | Oakley | |
| 7,072,668 B2 | 7/2006 | Chou | |
| 7,091,915 B1 | 8/2006 | Truthan | |
| 7,133,697 B2 | 11/2006 | Judd | |
| 7,196,621 B2 | 3/2007 | Kochis | |
| 7,265,668 B1 | 9/2007 | Brosius | |
| 7,265,970 B2 | 9/2007 | Jordan | |
| 7,356,390 B2 | 4/2008 | Knoblach | |
| 7,558,057 B1 | 7/2009 | Naksen | |
| 7,660,345 B2 | 2/2010 | Yu | |
| 7,743,999 B1 | 6/2010 | Griffin | |
| 7,791,312 B2 | 9/2010 | Kook | |
| 7,936,147 B2 | 5/2011 | Kook | |
| 8,035,577 B2 | 10/2011 | Lafarre | |
| 8,328,055 B1 | 12/2012 | Snyder | |
| 8,432,258 B2 | 4/2013 | Wilkinson | |
| 8,511,606 B1 | 8/2013 | Lutke | |
| 8,605,421 B2 | 12/2013 | Verschoor | |
| 8,676,334 B2 | 3/2014 | Youn | |
| 8,826,046 B2 | 9/2014 | Lu | |
| 8,831,601 B2 | 9/2014 | Mitchell | |
| 8,880,241 B2 | 11/2014 | Mohamadi | |
| 8,896,992 B2 | 11/2014 | Sherlock | |
| 8,902,777 B1 | 12/2014 | Huang | |
| 8,929,085 B2 | 1/2015 | Franklin | |
| 9,086,847 B2 | 7/2015 | Filipovic | |
| 9,130,651 B2 | 9/2015 | Tabe | |
| 9,207,715 B2 | 12/2015 | Filipovic | |
| 9,331,875 B2 | 5/2016 | Ashrafi | |
| 9,369,370 B2 | 6/2016 | Chow | |
| 9,374,788 B2 | 6/2016 | Singamsetti | |
| 9,387,940 B2 | 7/2016 | Godzdanker | |
| RE46,111 E | 8/2016 | Kook | |
| 9,413,501 B2 | 8/2016 | Kamijoh | |
| 9,481,458 B2 | 11/2016 | Casado Magana | |
| 9,504,099 B2 | 11/2016 | McGuire | |
| 9,525,524 B2 | 12/2016 | Barzegar | |
| 9,537,345 B2 | 1/2017 | Wang | |
| 9,554,751 B2 | 1/2017 | Filipovic | |
| 9,622,133 B1 | 4/2017 | Guvenc | |
| 9,624,706 B2 | 4/2017 | Jacobs | |
| 9,629,220 B2 | 4/2017 | Raptopoulos | |
| 9,641,208 B2 | 5/2017 | Sela | |
| 9,671,835 B2 | 6/2017 | Filipovic | |
| 9,773,601 B2 | 9/2017 | Breiwa | |
| 9,847,944 B2 | 12/2017 | Chow | |
| 9,885,451 B2 | 2/2018 | Spiro | |
| 9,918,673 B2 | 3/2018 | Dugan | |
| 9,938,008 B2 | 4/2018 | Stabler | |
| 9,986,440 B2 | 5/2018 | Guvenc | |
| 9,999,038 B2 | 6/2018 | Barzegar | |
| 10,014,948 B2 | 7/2018 | Ashrafi | |
| 10,020,891 B2 | 7/2018 | Ashrafi | |
| 10,064,095 B2 | 8/2018 | Kerpez | |
| 10,124,908 B2 | 11/2018 | Stabler | |
| 10,153,845 B2 | 12/2018 | Ashrafi | |
| 10,159,430 B1 | 12/2018 | Filipovic | |
| 10,187,156 B2 | 1/2019 | Ashrafi | |
| 10,192,665 B2 | 1/2019 | Breiwa | |
| 10,244,098 B2 | 3/2019 | Muthukumar | |
| 10,247,715 B2 | 4/2019 | Rossignol | |
| 10,313,164 B2 | 6/2019 | Mody | |
| 10,326,488 B2 | 6/2019 | Wojcik | |
| 10,374,710 B2 | 8/2019 | Ashrafi | |
| 10,425,159 B2 | 9/2019 | Leiba | |
| 10,437,295 B1 | 10/2019 | Filipovic | |
| 10,448,276 B2 | 10/2019 | Chun | |
| 10,530,479 B2 | 1/2020 | Chow | |
| 10,666,348 B1* | 5/2020 | Legare | H01Q 21/22 |
| 10,784,962 B2 | 9/2020 | Ashrafi | |
| 2003/0104781 A1 | 6/2003 | Son | |
| 2003/0115475 A1 | 6/2003 | Russo | |
| 2004/0038644 A1 | 2/2004 | Jimenez | |
| 2004/0066326 A1 | 4/2004 | Knapp | |
| 2004/0110469 A1 | 6/2004 | Judd | |
| 2004/0184466 A1 | 9/2004 | Chang | |
| 2004/0192227 A1 | 9/2004 | Beach | |
| 2004/0246891 A1 | 12/2004 | Kay | |
| 2005/0110640 A1 | 5/2005 | Chung | |
| 2005/0221764 A1 | 10/2005 | Shen | |
| 2006/0050475 A1 | 3/2006 | Chen | |
| 2006/0071864 A1 | 4/2006 | Richard | |
| 2006/0084379 A1 | 4/2006 | O'Neill | |
| 2006/0152344 A1 | 7/2006 | Mowery | |
| 2007/0171888 A1 | 7/2007 | Adams | |
| 2007/0237242 A1 | 10/2007 | Gjertsen | |
| 2008/0149403 A1 | 6/2008 | Fein | |
| 2008/0150295 A1 | 6/2008 | Fein | |
| 2008/0163919 A1 | 7/2008 | Fein | |

(56) References Cited

U.S. PATENT DOCUMENTS

| | | |
|---|---|---|
| 2008/0131893 A1 | 8/2008 | Maraganore |
| 2008/0252537 A1 | 10/2008 | Petros |
| 2009/0021435 A1 | 1/2009 | Shin |
| 2009/0086655 A1 | 4/2009 | Ghadaksaz |
| 2009/0099761 A1 | 4/2009 | Davis |
| 2009/0147758 A1 | 6/2009 | Kumar |
| 2009/0156141 A1 | 6/2009 | Sulc |
| 2009/0261778 A1 | 10/2009 | Kook |
| 2009/0294576 A1 | 12/2009 | LaForge |
| 2009/0325511 A1* | 12/2009 | Kim ............... G01D 21/00 455/84 |
| 2010/0128671 A1 | 5/2010 | Chen |
| 2010/0207572 A1 | 8/2010 | Kirby |
| 2010/0218224 A1 | 8/2010 | Gat |
| 2010/0231163 A1 | 9/2010 | Machinsky |
| 2010/0289450 A1 | 11/2010 | Kook |
| 2010/0292877 A1 | 11/2010 | Lee |
| 2011/0043301 A1 | 2/2011 | Huettner |
| 2011/0084162 A1 | 4/2011 | Goossen |
| 2011/0140656 A1 | 6/2011 | Starr |
| 2011/0169451 A1 | 7/2011 | Stampfli |
| 2011/0202221 A1 | 8/2011 | Sobue |
| 2011/0222448 A1 | 9/2011 | Ofek |
| 2011/0250819 A1 | 10/2011 | Tashman |
| 2012/0015603 A1 | 1/2012 | Proctor, Jr. |
| 2012/0068896 A1 | 3/2012 | White |
| 2012/0088557 A1 | 4/2012 | Liang |
| 2012/0120243 A1 | 5/2012 | Chien |
| 2012/0158229 A1 | 6/2012 | Schaefer |
| 2012/0212896 A1 | 8/2012 | Schulz |
| 2012/0213254 A1 | 8/2012 | Yokouchi |
| 2012/0218695 A1 | 8/2012 | Sakai |
| 2012/0235635 A1 | 9/2012 | Sato |
| 2012/0241247 A1 | 9/2012 | Choe |
| 2012/0247989 A1 | 10/2012 | Cooper |
| 2012/0249064 A1 | 10/2012 | Negishi |
| 2012/0249388 A1 | 10/2012 | Hansen |
| 2012/0252411 A1 | 10/2012 | Johnsgard |
| 2012/0262345 A1 | 10/2012 | Byun |
| 2012/0268891 A1 | 10/2012 | Cencioni |
| 2012/0270600 A1 | 10/2012 | Zelson |
| 2012/0281356 A1 | 11/2012 | Brewer |
| 2012/0299966 A1 | 11/2012 | Kim |
| 2013/0063873 A1 | 3/2013 | Wodrich |
| 2013/0076614 A1 | 3/2013 | Ive |
| 2013/0081245 A1 | 4/2013 | Vavrina |
| 2013/0093388 A1 | 4/2013 | Partovi |
| 2013/0143594 A1 | 6/2013 | Ghabra |
| 2013/0147330 A1 | 6/2013 | DiFonzo |
| 2013/9141299 | 6/2013 | Mast |
| 2013/0200703 A1 | 8/2013 | Liao |
| 2013/0217445 A1 | 8/2013 | Chan |
| 2013/0221757 A1 | 8/2013 | Cho |
| 2013/0288600 A1 | 10/2013 | Kuusilinna |
| 2014/0032034 A1 | 1/2014 | Raptopoulos |
| 2014/0085815 A1 | 3/2014 | Filipovic |
| 2014/0086586 A1 | 3/2014 | Voutilainen |
| 2014/0087788 A1 | 3/2014 | Filipovic |
| 2014/0159673 A1 | 6/2014 | Han |
| 2014/0159867 A1 | 6/2014 | Sartee |
| 2014/0172194 A1 | 6/2014 | Levien |
| 2014/0172354 A1 | 6/2014 | Chu |
| 2014/0203939 A1 | 7/2014 | Harrington |
| 2014/0273892 A1 | 9/2014 | Nourbakhsh |
| 2014/0274084 A1 | 9/2014 | Ross |
| 2014/0285159 A1 | 9/2014 | Wang |
| 2014/0334098 A1 | 11/2014 | Lauder |
| 2014/0376370 A1 | 12/2014 | Cioffi |
| 2015/0016330 A1 | 1/2015 | Schwartz |
| 2015/0035437 A1 | 2/2015 | Panopoulos |
| 2015/0123496 A1 | 5/2015 | Leabman |
| 2015/0130290 A1 | 5/2015 | Park |
| 2015/0141093 A1 | 5/2015 | Sela |
| 2015/0158599 A1 | 6/2015 | Sisko |
| 2015/0181413 A1 | 6/2015 | Singamsetti |
| 2015/0200722 A1 | 7/2015 | Kang |
| 2015/0237706 A1 | 8/2015 | Ben-Moshe |
| 2015/0289147 A1 | 10/2015 | Lou |
| 2015/0301168 A1 | 10/2015 | Brown |
| 2015/0303586 A1 | 10/2015 | Pan |
| 2016/0106370 A1 | 4/2016 | Filipovic |
| 2016/0221688 A1 | 8/2016 | Moore |
| 2016/0262113 A1 | 9/2016 | Diamond |
| 2016/0294427 A1 | 10/2016 | Wojcik |
| 2016/0360511 A1 | 12/2016 | Barzegar |
| 2017/0011333 A1 | 1/2017 | Grainer |
| 2017/0068290 A1 | 3/2017 | Filipovic |
| 2017/0118688 A1 | 4/2017 | Guvenc |
| 2017/0122546 A1 | 5/2017 | Abbott |
| 2017/0171761 A1 | 6/2017 | Guvenc |
| 2017/0195054 A1 | 7/2017 | Ashrafi |
| 2017/0238301 A1 | 8/2017 | Nakazawa |
| 2017/0366270 A1 | 12/2017 | Ashrafi |
| 2018/0026722 A1 | 1/2018 | Ashrafi |
| 2018/0123692 A1 | 5/2018 | Leiba |
| 2018/0124330 A1 | 5/2018 | Muthukumar |
| 2018/0139797 A1 | 5/2018 | Chun |
| 2018/0248596 A1* | 8/2018 | Xiao ............... H04L 25/0204 |
| 2018/0262272 A1 | 9/2018 | Ashrafi |
| 2018/0278334 A1 | 9/2018 | Ashrafi |
| 2018/0294866 A1 | 10/2018 | Ashworth |
| 2019/0002129 A1 | 1/2019 | Walsh |
| 2019/0036209 A1 | 1/2019 | Au |
| 2019/0082495 A1 | 3/2019 | Kim |
| 2019/0089452 A1* | 3/2019 | Ashworth ......... H04B 7/15571 |
| 2019/0173582 A1 | 6/2019 | Ashrafi |
| 2019/0221353 A1 | 7/2019 | Hwang |
| 2019/0223235 A1 | 7/2019 | Schwartz |
| 2022/0141776 A1 | 5/2022 | Diamond |

* cited by examiner

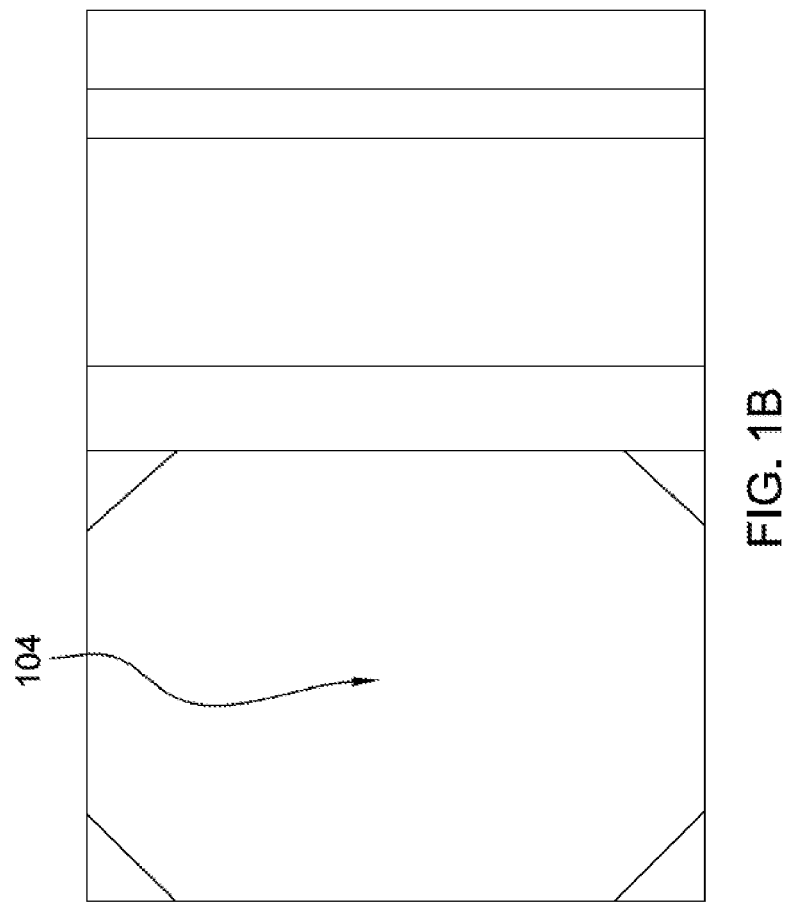
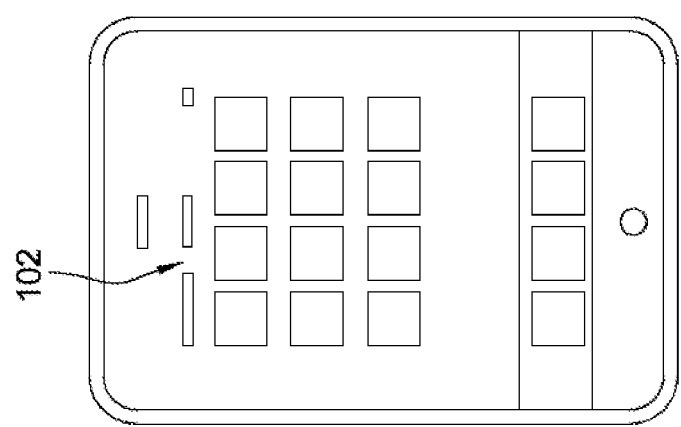

| | | | | |
|---|---|---|---|---|
| Y | Y | Y | ... | N |
| Y | Y | Y | ... | N |
| Y | Y | Y | ... | N |
| : | : | : | | |
| N | N | N | ... | N |

US 11,553,857 B1

SYSTEM AND METHOD FOR THROUGH WINDOW PERSONAL CLOUD TRANSMISSION

PRIORITY CLAIM

This patent application claims priority as a non-provisional of U.S. Provisional Patent Application 62/968,147, filed on Jan. 30, 2020 and as a Continuation-In-Part of U.S. patent application Ser. No. 16/595,914, filed on Oct. 8, 2018; which claim priority as a non-provisional of U.S. Provisional Patent Application 62/757,052, filed on Nov. 7, 2018 and as a Continuation-In-Part of U.S. patent application Ser. No. 15/614,555, filed on Jun. 5, 2017; which claims priority as a Continuation-In-Part of U.S. patent application Ser. No. 14/803,828, filed on Jul. 20, 2015; which claims priority as a Continuation of U.S. patent application Ser. No. 13/831,663, filed on Mar. 15, 2013; which claims the benefit of U.S. Provisional Patent Application Ser. No. 61/705,383, filed Sep. 25, 2012; the aforementioned applications all being incorporated herein by reference in their entirety.

FIELD OF THE DISCLOSURE

The present disclosure relates generally to portable electronic devices and antenna arrays and, in particular, the present disclosure relates to an always on radio frequency (RF) communication device.

BACKGROUND

There are presently a wide variety of portable electronic devices 102 as disclosed in FIG. 1A. The portable electronic devices may include cellphones such as the iPhone®, Nexus, Lumia and the like and tablet personal computers (PCs) such as the iPad®, Kindle® and similar type devices. These portable electronic devices are often protected by a simple case cover 104 as disclosed in FIG. 1B. These prior art case covers 104 typically do not contain any functional components beyond the protective cover itself.

SUMMARY

Aspects of the disclosure include a communication device comprising: a downlink path having a low noise amplifier in an on state; a first antenna in an uplink path capable of receiving a first signal at a first frequency and coupled to a receive signal detector and amplifier (RSDA); a controller capable of receiving an indication from the RSDA that the first signal has been received and automatically turning on the uplink path by activating a power amplifier and turning off the downlink path by turning off the low noise amplifier; and the power amplifier capable of amplifying the first signal and sending the first signal to a second antenna which is capable of transmitting the first signal at the first frequency.

Aspects of the disclosure further include a communication device comprising: a downlink path having a low noise amplifier in an on state; a first antenna in an uplink path capable of receiving a first signal at a first frequency and coupled to a receive signal detector and amplifier (RSDA); a controller capable of receiving an indication from the RSDA that the first signal has been received and automatically turning on the uplink path by activating a power amplifier and turning off the downlink path by turning off the low noise amplifier; wherein the controller operates a phase shifter and antenna array to steer the transmit and receive direction of the antenna and direct the alignment of the first signal; and the power amplifier capable of amplifying the first signal and sending the first signal to a second antenna which is capable of transmitting the first signal at the first frequency.

BRIEF DESCRIPTION OF THE DRAWINGS

FIG. 1A is a front view of a prior art mobile computing device.

FIG. 1B is a front view of a prior art simple case cover for a mobile computing device.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Current mobile computing device covers are limited in their functionality by mainly providing protection from environmental shocks for mobile computing devices. However, the personal cloud cover case (or "PCCC") as disclosed in this application by providing electronic component accessories and functionalities to the cover case enhances the ability of a mobile computing device located inside the PCCC to provide cloud computing services. Cloud computing is the use of computing resources that are delivered as a service over a network (such as the Internet) and which reside in the "cloud". The mobile computing device in the case could be an iPad®, iPhone®, PC tablet, Android® based tablet, TouchPad, Nexus 7®, Slate® or the like.

Figure 2A:
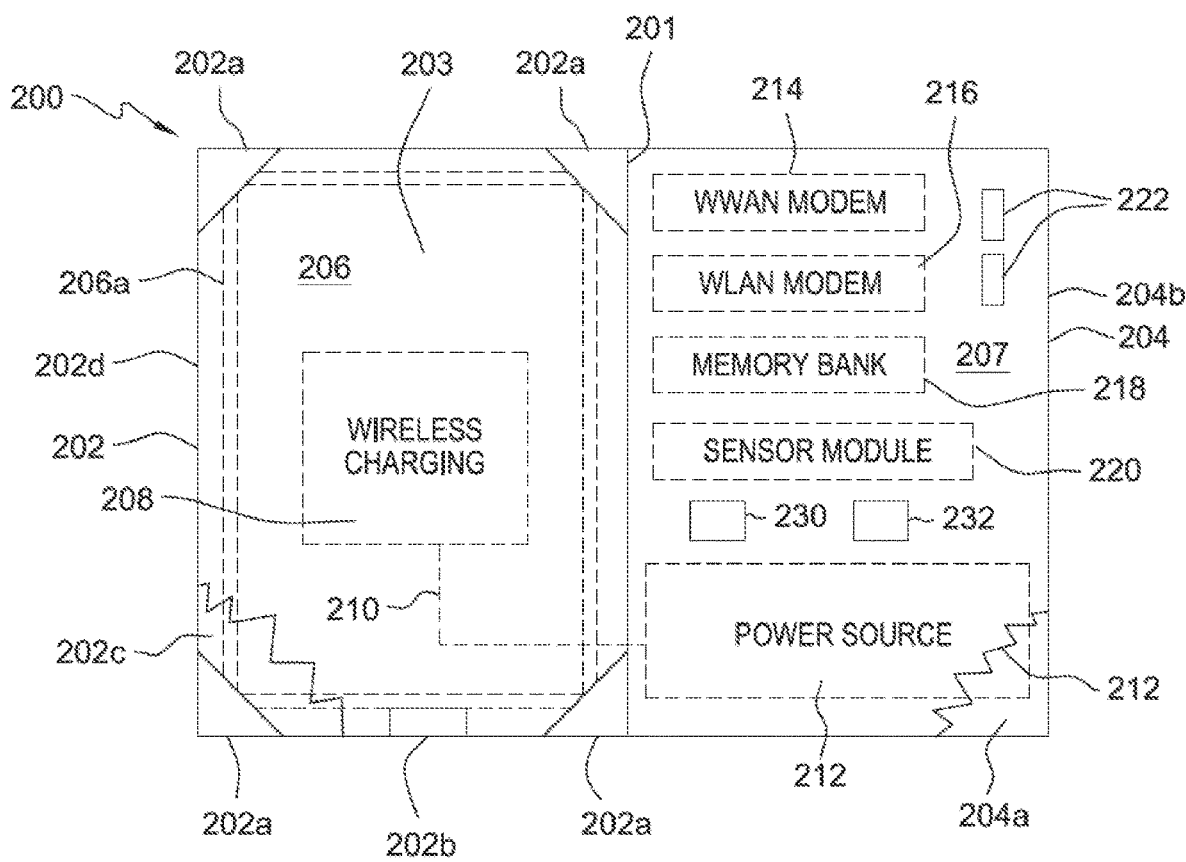
FIG. 2A is a front view of a personal cloud case cover (PCCC).

FIG. 2A is a front view of a PCCC 200 which is shown in an open position. The case 200 provides a personal cloud to the user and access to a wireless network (such as 3G, 4G, 5G, WiFi, SuperWifi, and similar technologies) of a mobile computing device (not shown) stored in the case 200. The case 200 may be made of any material (hard and/or soft) that makes the case lightweight but durable and resilient such as plastic, silicone, ceramic, fabric, leather, steel, aluminum, fiberglass, titanium, Kevlar, or rubber. The case 200 could be a continuous piece of material with a flexible (or bendable) area 201 located between two opposing panels (first panel 202 and second panel 204) which pivot together around a compartment 203 for containing the mobile computing device. In an alternative embodiment, the case 200 could be made up of plurality of attached sections (201, 202 and 204). First panel 202 also has 4 sleeves 202a to hold the mobile computing device in place in the case 200. In alternative embodiments, the mobile computing device could be attached to the PCCC 200 using a plurality of magnets (instead of the sleeves 202a) positioned under the mobile device, rubber straps or other similar attachment methods.

The first panel 202 is constructed in layers and includes inner first panel layer 202c, outer first panel layer 202d and embedded circuit board 206. Typically, from the front view the circuit board 206 cannot be seen since it is located underneath the first panel layer 202c shown in cutaway but which is designed to cover substantially the entire first panel 202. An antenna 206a is located on the circuit board 206 and may be in contact with the mobile communication device wirelessly, through physical contact or by connector 202b. Connector 202b is optional and in alternative embodiments it would not be present. The antenna 206a will allow for better transmission and reception on the part of the mobile communication device. The antenna 206a can be a "chip" antenna, printed circuit board (PCB) antenna or the like covering a plurality of wireless bands (e.g., 400 MHz-3.6 GHz). Alternatively, a PCB antenna may be used, and the antenna 206a will be printed directly onto the circuit board 206. Also located on the board 206 is a two-way wireless charging unit 208 which is in substantial proximity to the resting place of the mobile communication device in the cover 200. The charging unit 208 is designed such that when the mobile communication device is in proximity to the charging unit an electromagnetic field generated by the charging unit pulls the communication device into proper position and alignment for optimal charging (i.e., charging coil alignment). The wireless charging unit 208 is connected through a bidirectional electrical link 210 to power source 212 located on a circuit board 207 embedded in the second panel 204. The bidirectional electrical link 210 is an example of the plurality of electrical connections that are made throughout the case 200 but which are not necessarily shown in the Figures. Link 210 might be in the form of a ribbon cable so as not to be damaged with the opening and closing of the case 200. The wireless charging unit 208 is capable of wirelessly charging the mobile communication device with power received from the power source 212 or wirelessly receive power from the mobile communication device and transfer it to the power source 212. The wireless charging unit 208 may operate by magnetic resonance, inductive charging, or power over radio frequency (RF) or similar wireless charging methods. The power source 212 is used to power the plurality of components located throughout the cover 200 and, as described, can also be used as a backup battery for the mobile computing device when the voltage in the battery of the mobile computing device falls below a predetermined level.

The second panel 204 can be made up of an inner second panel 204a and an outer second panel 204b containing the embedded circuit board 207 but which typically cannot be seen from a front view since it is covered by inner second panel layer 204a. The inner second panel layer 204a covers substantially the entire second panel 204 but is only partially shown in cutaway so as to illustrate the components mounted on the circuit board 207 in the outer second panel 204b. It should be understood that the inner second panel layer 204a and the outer second panel layer 204b can be coupled together by a variety of methods such as ultrasonic bonding, mechanical fasteners, adhesives, or solvents. In alternative embodiments, the inner second panel 204a may be entirely or substantially detachable from the outer second panel 204b; the inner second panel 204a may be a closure flap that is fastened close by means of adhesive, a snap button, or Velcro or the inner second panel 204a may not be present at all so as to allow easy access to the components mounted on the board 207 in the outer second panel 204b. The case 200 may further be made up of a plurality of modules 214, 216, 218 and 220 mounted on the circuit board 207 which allow the PCCC 200 to have multi-functional capability. The modules may be made of low profile components which help minimize the thickness of the cover. The plurality of modules may be permanently mounted, may snap-in to the board 207 or may be some combination thereof. First module 214 may include a wireless wide area network modem (WWAN). The WWAN could include baseband, a radio frequency integrated circuit (RFIC), a radio frequency front-end module (RF FEM), Envelope Tracking (ET), Power Management IC (PMIC), and other connected components to link the mobile computing device to a mobile network such as a 3G, 4G or future generation network. Second module 216 may include a wireless local area network (WLAN) modem for a mobile computing device to connect to a local router and then to 2G, 3G and 4G networks. The WLAN modem can be baseband, RFIC, RF FEM and other connectivity components. The case 200 may contain near field communications (NFC) technology which may be used for contactless short range communications based on RF identification standards (RFID) using magnetic field induction to enable communication between the electronic components in the case 200 over short distances such as a few centimeters. In other embodiments, the WLAN modem connection could be made using wireless protocols such as WiFi, SuperWiFi (i.e., the next generation WiFi with superior range), Bluetooth, wireless for high definition multimedia interface (WHDMI), or the like. Third module 218 may be internal storage such as solid-state drives (SSD) or flash memory (e.g., MultiMedia Card (MMC), electronic MMC (eMMC) or the like). Fourth module 220 may contain a sensor chip that is able to detect biometrics inputs such as finger prints, eye movement, face shape, and the like. Module 220 can be used for functions such as a security feature for allowing or denying access to the electronic components in the case, gaming, and medical purposes (e.g., measuring blood cell count and the like). The second panel 204 may also include a smart feature such as a synchronization input 230 (e.g., such as a button, touch screen, or the like) that allows the plurality of electronic components (e.g., module 218) in the PCCC 200 to be synched to other networked devices in the cloud when operated. This input 230 would primarily be used when a mobile communication device is not present in the PCCC 200. The input 230 may be used to backup data stored in the components of the PCCC 200. Reference 232 in FIG. 2A shows a controller which may be used with the mobile communication device or in the absence of the mobile device to control the electronic components in the PCCC 200. For example, in the synching process when input 230 is operated the controller 232 would direct the synching operation.

Figure 2B:
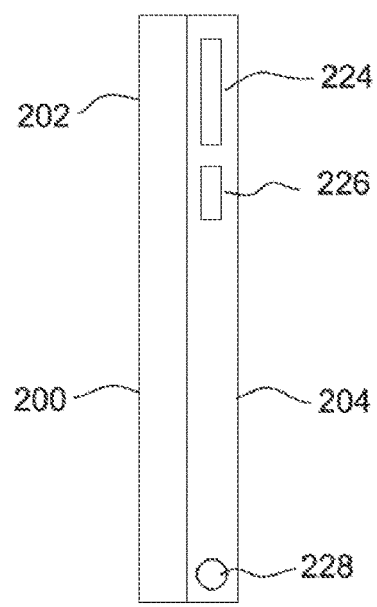
FIG. 2B is a side view of the PCCC of FIG. 2A.

FIG. 2B is a side view of the case 200 in a closed position. Data connection ports 224 and 226 provide communication capabilities to the case 200. Ports 224 and 226 may be a mini universal serial bus (USB), micro universal USB port or an audio visual (AV) connector such as a high definition multimedia interface (HDMI) port and the like. Charging port 228 can be connected to the grid or other power source to feed the power source 212.

Figure 3:
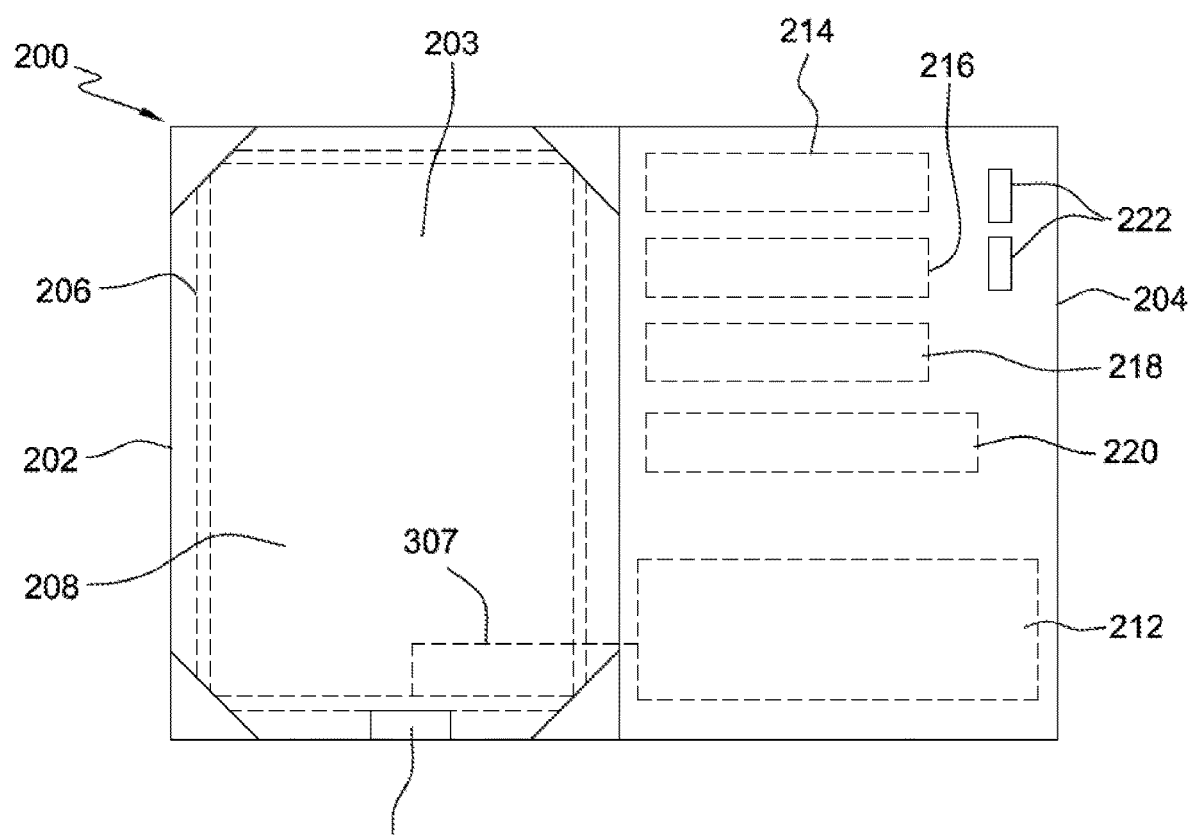
FIG. 3 is a front view of a second embodiment of the PCCC.

FIG. 3 is a second embodiment of the PCCC 200. Common numbering is used in FIGS. 3 though 9 and FIGS. 2A to 2B to denote similar elements. In this second embodiment, instead of wireless charging, a docking bay 305 having a set of electrical contacts is configured to electrically engage with the input/output contacts on a mobile communication device. The docking bay 305 may be a standard connector that allows the mobile communication device to receive power through line 307 from power source 217.

Figure 4:
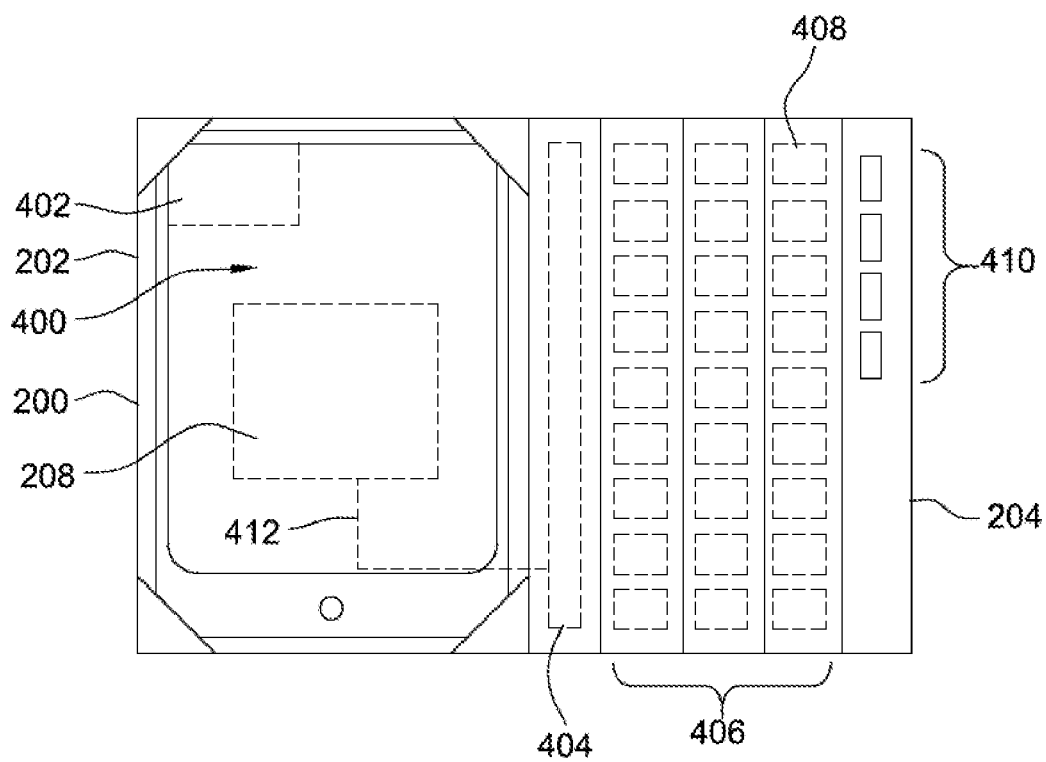
FIG. 4 is a front view of a third embodiment of the PCCC.

FIG. 4 illustrates a third embodiment of the PCCC 200. A mobile communication device 400 can be connected to a local area or wide area network through wireless modem 402 which may be 3G, 4G, 3G/4G, 5G, WHDMI, Bluetooth, WiFi, SuperWiFi, and other wireless standard. Module 404 is a replaceable, rechargeable battery that is charged through line 412 from the wireless charger 208 and receives power from mobile communication device 400. Module 404 performs the same function as power source 212 in FIG. 2 but is arranged differently in the case 200 as shown in FIG. 4. The wireless charger 208 may be located on the first panel 202 beneath the mobile communications device 400. The module 404 can also be charged from a power outlet when the case 200 is plugged in. The module 404 can be used as a power source for other modules (reference numerals 408 and 410 as discussed below) located in the case 200. An embedded memory bank 406 includes a plurality of memory modules and is mounted on the second panel 204. The memory bank modules may be 500 MegaByte (MB), 1 Gigabyte (GB), 1 Terrabyte (TB) or the like in memory size. Memory slots 410 are capable of holding additional memory such as removable micro-Secure Digital (micro-SD) memory cards for storage expansion.

Figure 5:
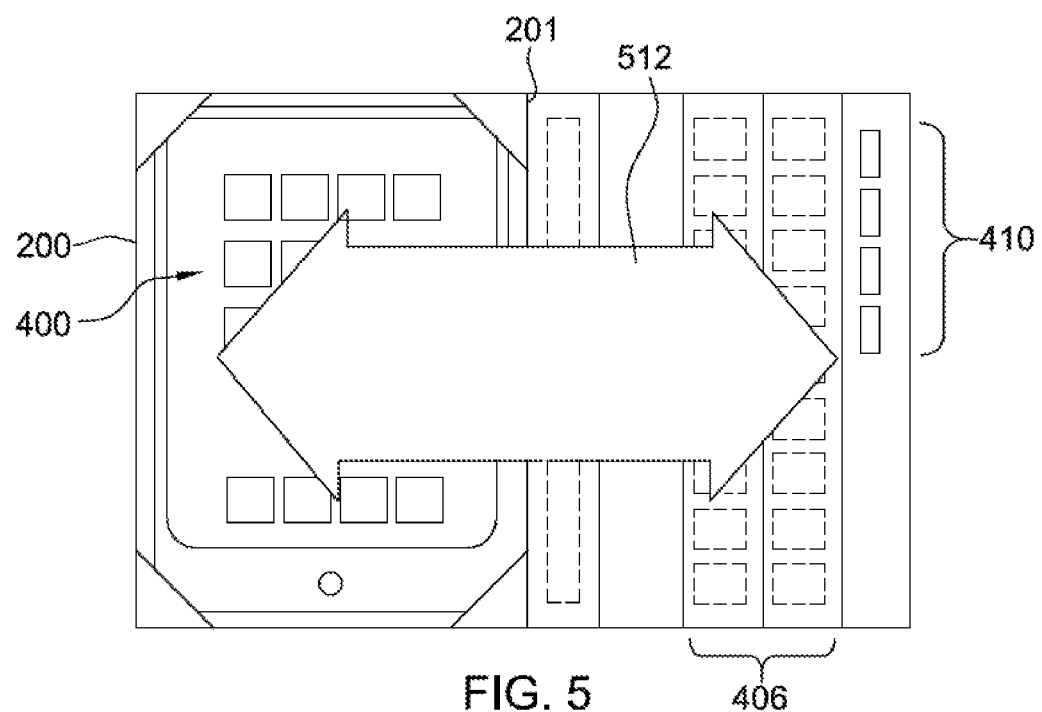
FIG. 5 is a front view of a fourth embodiment of the PCCC.

FIG. 5 illustrates a fourth embodiment of the PCCC 200 which demonstrates that the plurality of modules are detachable and could be two instead of three in the case 200. Also, FIG. 5 discloses a wireless data connection 512 between the device 400 and memory bank 406 using WiFi, SuperWiFi or Bluetooth protocols. In alternate embodiments, the data connection 512 could be a hardwired such as a Universal Serial Bus (USB), microUSB, miniUSB, or HDMI (with the data line being flexibly bendable across the flexible region 201 in the form of a ribbon cable or the like). In other embodiments, the connection could also be an optical wireless link or cable such as infrared. The data transfer could be bi-directional to allow for read and write both ways from device 400 to memory 406 and from memory 406 to device 400.

Figure 6A:
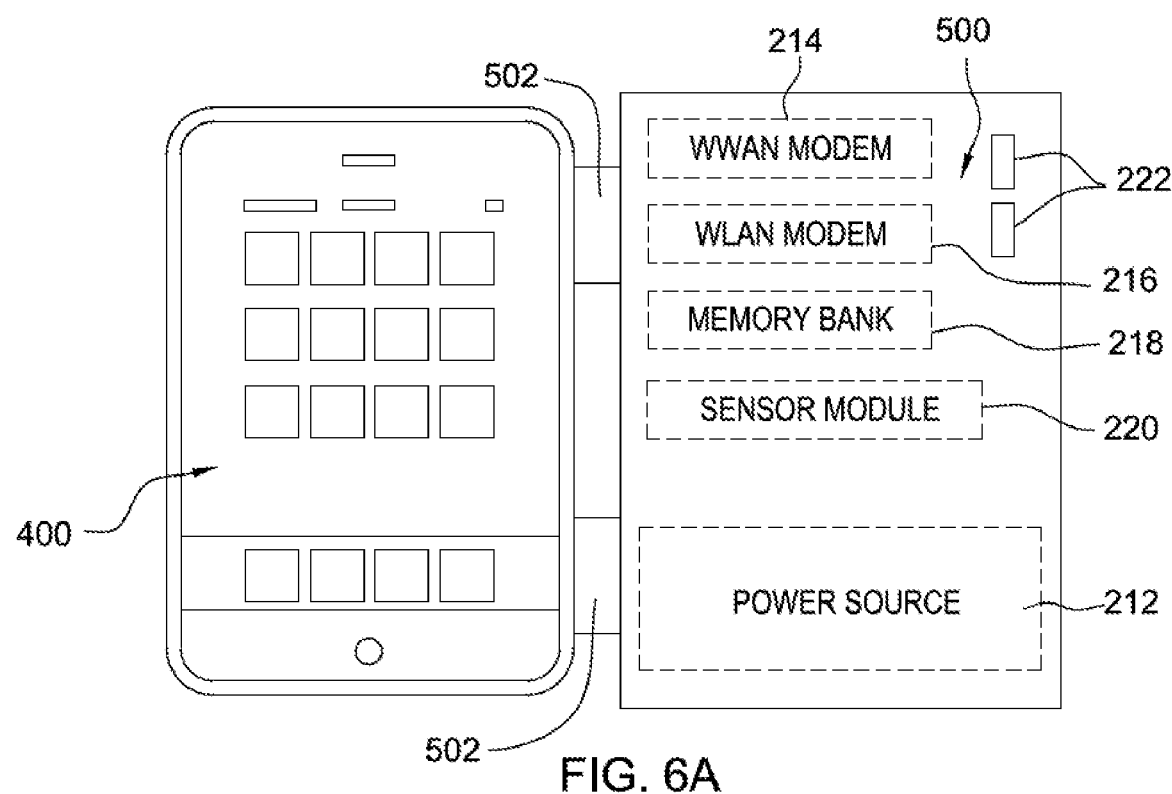
FIG. 6A is a front view of a fifth embodiment of the PCCC.
Figure 6B:
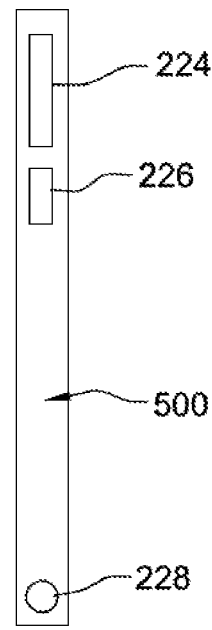
FIG. 6B is a side view of the PCCC of FIG. 6A.

FIG. 6A is another embodiment of the PCCC with just one panel 500 attached to the device 400 through attachments 502. Attachments 502 may be magnets, clip ins, connectors or some other type of hinge. The attachments 502 may internally include a plurality of electrical links to provide power from the power source 212 to the mobile communication device 400 as well as provide data communications between the modules on the panel 500 and the device 400. The power source 212 may include a wireless charging unit so as to wirelessly charge the device 400. The charging may take place when the panel 500 is in a lateral position relative to the device 400 as shown in FIG. 6A. In an alternative embodiment, the panel 500 may be folded over and placed in contact with the device 500 to establish an electrical power link between the power source 212 and electrical contacts located on the device 400. Also, similar to the embodiment of FIG. 5, a wireless data connection may be established between the device 400 and the plurality of modules on the panel 500 (items 214, 216, 218, 220, and 222). FIG. 6B is a side view of the panel 500 showing the connection ports 224, 226, and 228 which serve the same functions as described in connection with FIG. 2B above.

Figure 7:
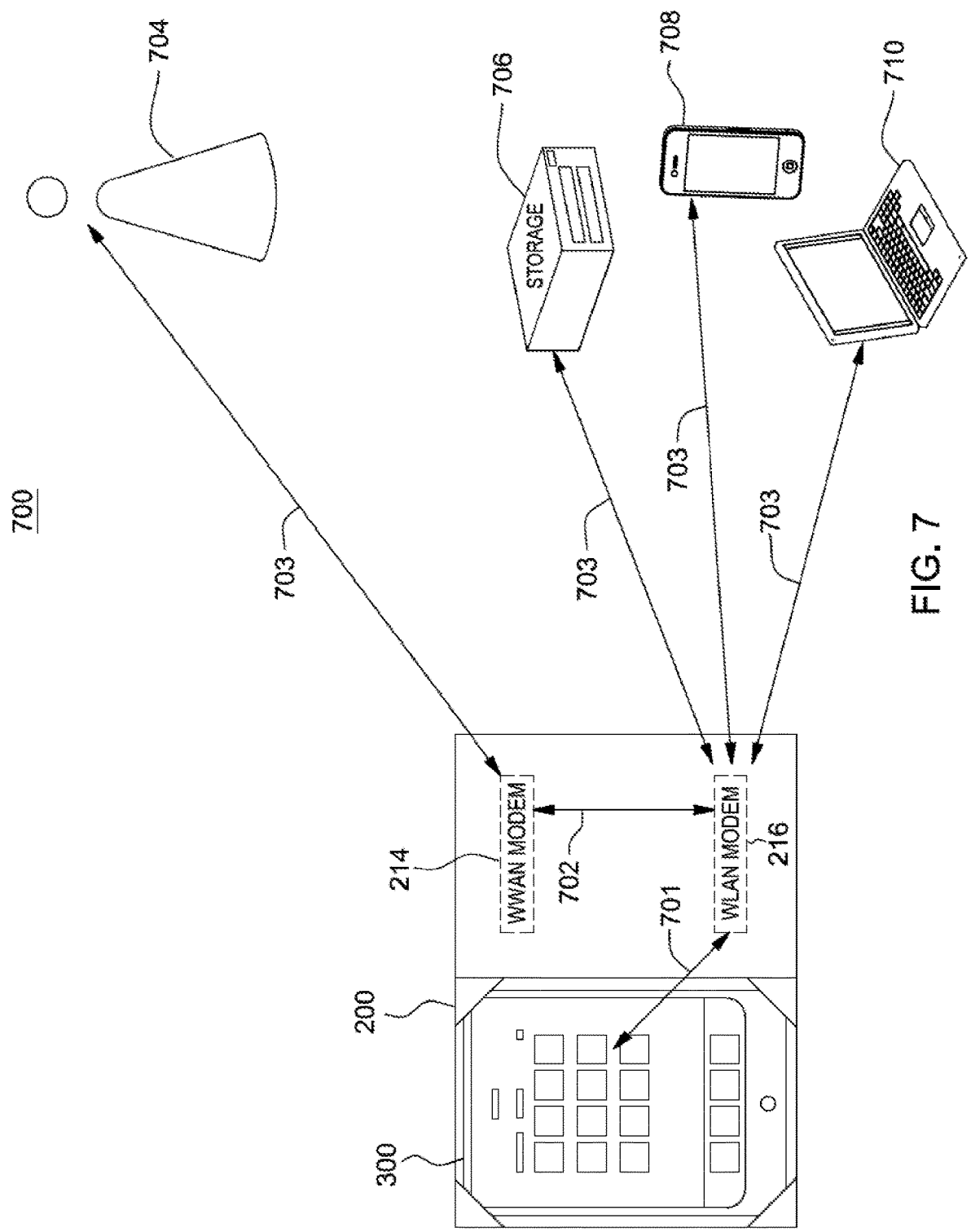
FIG. 7 is a schematic diagram of a PCCC in a cloud/networked environment utilizing 3rd Generation (3G), 4th Generation (4G), Fifth Generation (5G) and similar wireless connections.

FIG. 7 illustrates the mobile communication device 300 and PCCC 200 operating in a cloud (or networked) environment 700. Storage 706, mobile phone 708 and personal computer (PC) 710 are part of the cloud upon which the mobile communications device 300 and PCCC 200 can exchange data and synchronize through a plurality of wireless links 703. The WWAN modem module 214 and the WLAN modem module 216 of FIG. 7 operate in a similar manner as described in connection with FIG. 2A above. The mobile computing device 300 communicates through a bi-directional wireless link 701 with the WLAN modem 216 using Bluetooth, WiFi, SuperWiFi and similar wireless standards. In another embodiment, the link 701 may be a wired link. WLAN modem 216 then can read and write wirelessly in a local environment with storage 706. The WLAN modem 216 can also communicate with another mobile phone 708 and PC 710. Alternatively, the mobile computing device 300 can communicate through WLAN 216 over a bi-directional link 702 with WWAN modem 214. WWAN modem 214 can communicate wirelessly using 3G/4G protocols over longer distances than the WLAN modem 216 with a cell tower 704 and then to the Internet. In the environment of FIG. 7, the case 200 is acting as "hotspot". As a hotspot, the case 200 offers network (e.g., Internet) access over the WWAN modem 214 or WLAN modem 216.

Figure 8:
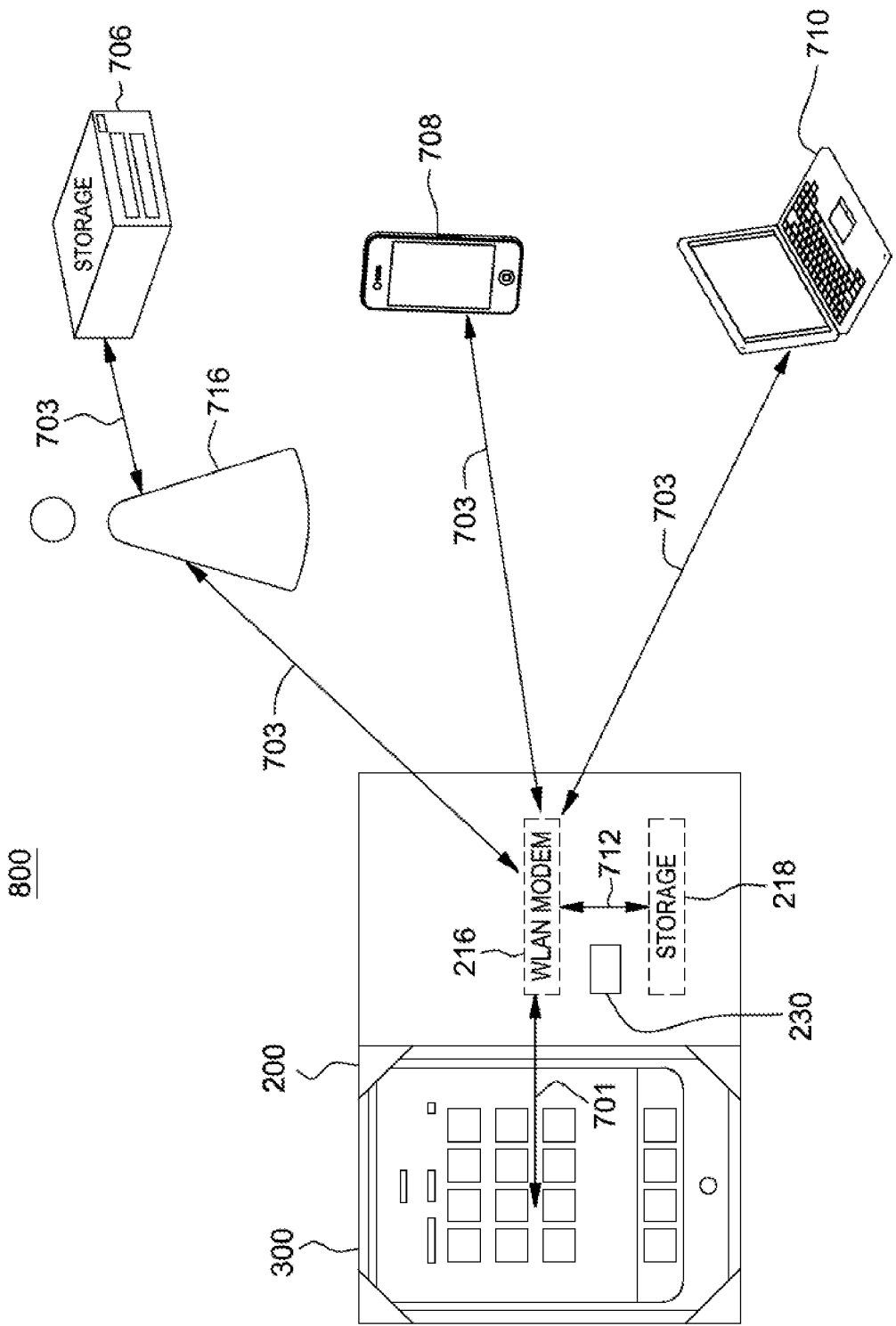
FIG. 8 is a schematic diagram of the PCCC in another cloud/networked environment system.

FIG. 8 illustrates another variation of the mobile communication device 300 and the case 200 in operation 800. This arrangement allows the local storage 218 to have access to a plurality of devices in the cloud such as the communication device 708, PC 710 and storage 706 through local wireless router (or access point) 716. As previously discussed in connection with FIG. 2A, sync input 230 can be operated when the mobile communication device is not present in the case 200 to backup all data contained in the components in the case 200 to the cloud (e.g., devices such as 706, 708, 710 and other devices). Another advantage is that this system allows for the formation of a "pass through Internet" from the mobile communication device 300 to devices 706, 708, 710 and a network (e.g., the Internet). WLAN modem 216 is connected to memory storage 218 through link 712 and is capable of establishing wireless communications with both the mobile communication device 300 and the devices 706, 708, and 710. In operation, the mobile communication device 300 establishes a wireless connection 701 through WiFi, SuperWiFi, 4G or the like to the WLAN modem 216. Through WLAN modem 216, the communication device 300 is capable of connecting to the memory storage 218 (e.g., providing information or instructions regarding reading and/or writing) while simultaneously browsing the Internet through wireless link 703 to access point 716. The term simultaneously as used herein shall mean immediate or nearly immediate succession in time. In another embodiment, the connection from the mobile communication device to the memory storage 218 could be wired. Alternatively, the communication device could be simultaneously connecting to memory storage 218 while communicating with devices 706, 708 and 710 through wireless links 703. This pass through Internet feature allows the user to access data stored in the memory 218 and browse the Internet simultaneously from a single device (mobile communication device 300) or a plurality of devices. The WLAN modem 216 is designed to operate in one or more bands and cover one or more wireless standards. The bands may include first and second frequency bands (e.g., 2 GHz and 5 GHz). The WLAN modem 216 may use the first band for the transmission of information from memory storage 218 to the mobile communication device 300 and the second band for communications with the access point 716 (and thereby the Internet).

Figure 9:
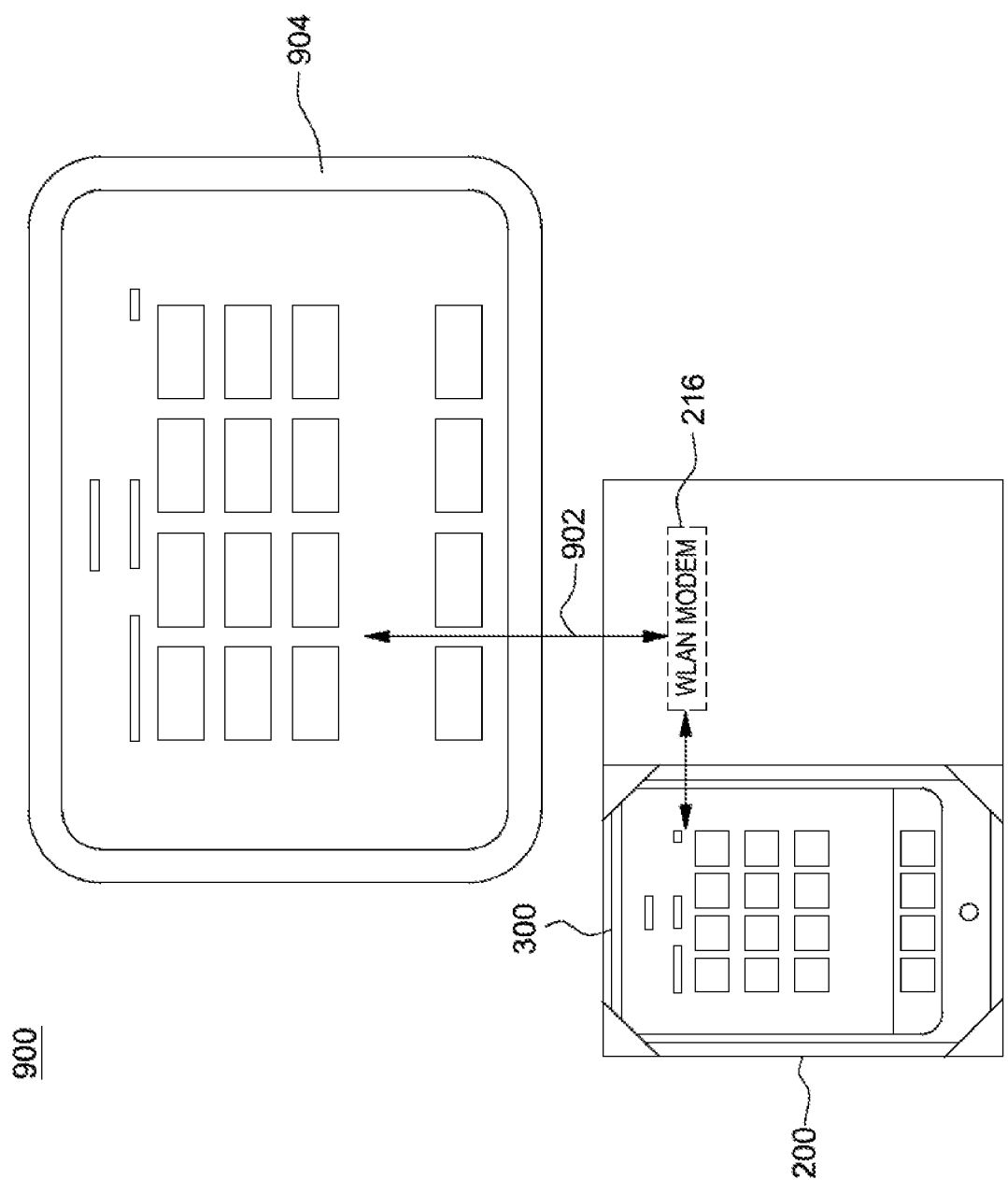
FIG. 9 is a view of the PCCC operating with a large external monitor.

FIG. 9 illustrates another environment 900 in which the PCCC 200 may operate. The PCCC 200 allows the mobile communication device 300 to link through WLAN 216 and wireless link 902 with large external monitor 904 using WiFi, SuperWiFi, WHDMI, or the like and display information (e.g., video, audio, or text) from either the mobile communication device 300, the memory storage or another source (e.g., devices 706, 708, 710) on to the monitor 904.

FIGS. 10-13B illustrate another environment 1000 in which the PCCC 200 may operate. As new wireless and fixed standards (such as 4G, 5G, 802.11ad, and the like) keep pushing the operating frequencies into millimeter (mm) wave spectrum (e.g., 28 GHz, 40 GHz, 60 GHz, 70 GHz, 100 GHz) it becomes harder and harder (due to higher penetration loss and path loss) to get the signal inside buildings, houses, cars, and even mobile phones (as phone casings might prevent millimeter wave signals from getting in or out). These challenges limit the usability of mm waves and make mm systems very expensive to deploy. The disclosed embodiments described herein help to make mm wave signal penetration possible.

In FIGS. 10-13B, PCCC 200 is an alternative embodiment in which an antenna array 240 is mounted in the case. (In alternative embodiments of FIGS. 10-13B it could be the one panel version of PCCC 500 shown in FIGS. 6A-6B used instead of the multiple panel version of the PCCC 200 but FIGS. 10-13B will use PCCC 200 for description purposes).

PCCC 200 can be any of the embodiments disclosed in FIGS. 1-9 which either further include antenna array 240 or where antenna array replaces elements and or modules of the PCCC 200 (or PCCC 500) disclosed in FIGS. 1-9. Antenna 240 can be a low cost antenna array 240 made up of cells in an N×N array (e.g. 2×2, 2×2, 4×4, 8×8, or the like) or an M×N array (e.g., 1×4, 2×4, 2×5, 2×8, or the like). The antenna array 240 could be made on circuit boards 206 or 207, it could be a chip antenna on the circuit boards 206 or 207, or it could be a multilayer antenna on the circuit boards 206 or 207. The antenna array 240 can be used to increase the gain of the signal 1004, can be used for beam forming and beam steering, phase shifting, and/or gesture tracking. The antenna array 240 may be in contact with the mobile communication device (not shown) wirelessly, through physical contact or through a connector (e.g., 202*b*) or an electrical link (or links) running through circuit boards 206 and 207. In alternative embodiments, the antenna array 240 could be attached to the side or back of the mobile communication device (such as when it is the form of embodiment PCCC 500) as well. The antenna array 240 may also be coupled to and controlled by the other elements and modules in the PCCC 200 (or PCCC 500) through electrical links in the circuit boards 206 and/or 207 and implemented using hardware, software, firmware, middleware, microcode, or any combination thereof. [0041] Antenna array 240 may be configured in a plurality of ways. Antenna 240 may be made up of cells in an N×N or M×N array configuration as discussed above. The array 240 may made of a low-cost material and a number of different substrates could be used each having their own fabrication tolerances and electrical and mechanical properties. The array 240 can be made of an Arion CLTE-XT (PTFE ceramic), a Rogers RT 5880/RO 3003 (PTFE glass fiber), a Rogers Liquid Crystal Polymer (LCP), a low temperature cofired ceramic (LTCC), a Parylene N dielectric, a polytetrafluoroethylene (PTFE) ceramic, a PTFE glass fiber material, a silicon material, a Gallium Arsenite (GaAs) material, an Alumina material, a Teflon material, a Duroid material or any other material that can produce thin (about 2-4 mils in thickness) metallized layers. In one embodiment, the layers may be stacked to form a multi-layer array architecture. With the antenna array 240 printed on a thin film material, mm wave signals can penetrate through any object efficiently and at low cost. The PCCC 200 surrounding array 240 may also be made of glass, plastic, etc.

Figure 10:
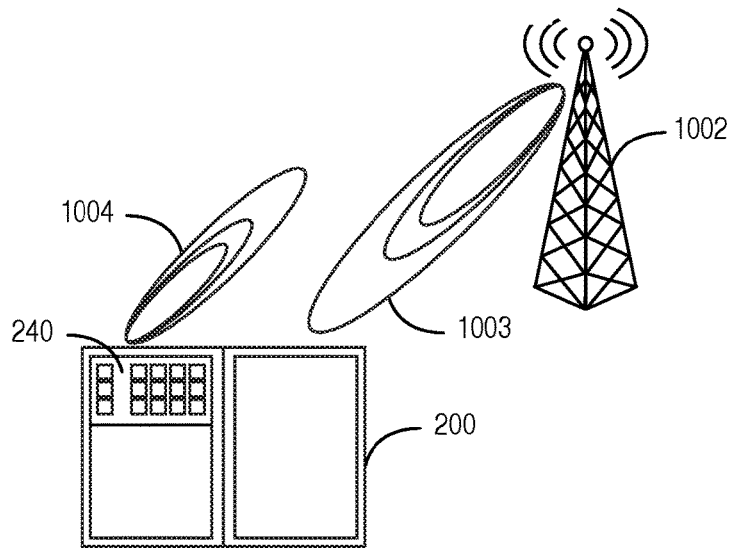
FIG. 10 is a PCCC 200 with an antenna array 240 in communication with a communication tower (e.g., cell tower, base station or the like) 1002 using millimeter (mm) wave signals 1003, 1004.

In FIG. 10, in operating environment 1000 antenna array 240 allows PCCC 200 to communicate with a communication tower (e.g., cell tower, base station or the like) 1002. Communication tower 1002 and antenna array 240 could communicate with each other using, for example, time domain (TDD) or frequency domain signals (FDD) 1002, 1003 (and 1302 as discussed below). Downlink signal (or beam) 1003 coming from communication tower 1002 and uplink signal (or beam) 1004 coming from array 240 are formed and steered to allow mm wave signal communications between the array 240 and communication tower 1002. The antenna array 240 may be located by communication tower 1002 using Global Positioning Satellite (GPS) technology or by 3G/4G/5G technology. Beams 1003 and 1004 (and 1302) may operate in the range of approximately 3 GigaHertz (GHz) to approximately 100 GHz or even higher. Typically, beams 1003 and 1004 (and 1302) will operate approximately in a range of plus or minus(+/−) 12% of mm wave frequency signals such as 24 GHz, 28 GHz, 39 GHz, 60 GHz, and/or 77 GHz (e.g., for 24 GHz the signal would range from approximately 21.12 GHz to approximately 26.88 GHz). Alternatively, mm wave beams 1003 and 1004 (and 1302) can operate in the following ranges: approximately 3.3 GHz to approximately 3.4 GHz; approximately 3.4 GHz to approximately 3.6 GHz; approximately 3.6 GHz to approximately 3.8 GHz; approximately 5.150 GHz to approximately 5.925 GHz; approximately 24.25 GHz to approximately 27.5 GHz; approximately 31.8 GHz to approximately 33.4 GHz; approximately 37.0 GHz to approximately 40.5 GHz; approximately 40.5 GHz to approximately 42.5 GHz; approximately 42.5 GHz to approximately 43.5 GHz; approximately 45.5 GHz to approximately 47 GHz; approximately 47.0 GHz to approximately 47.2 GHz; approximately 47.2 GHz to approximately 50.2 GHz; and approximately 50.4 GHz to approximately 52.8 GHz.

Figure 11:
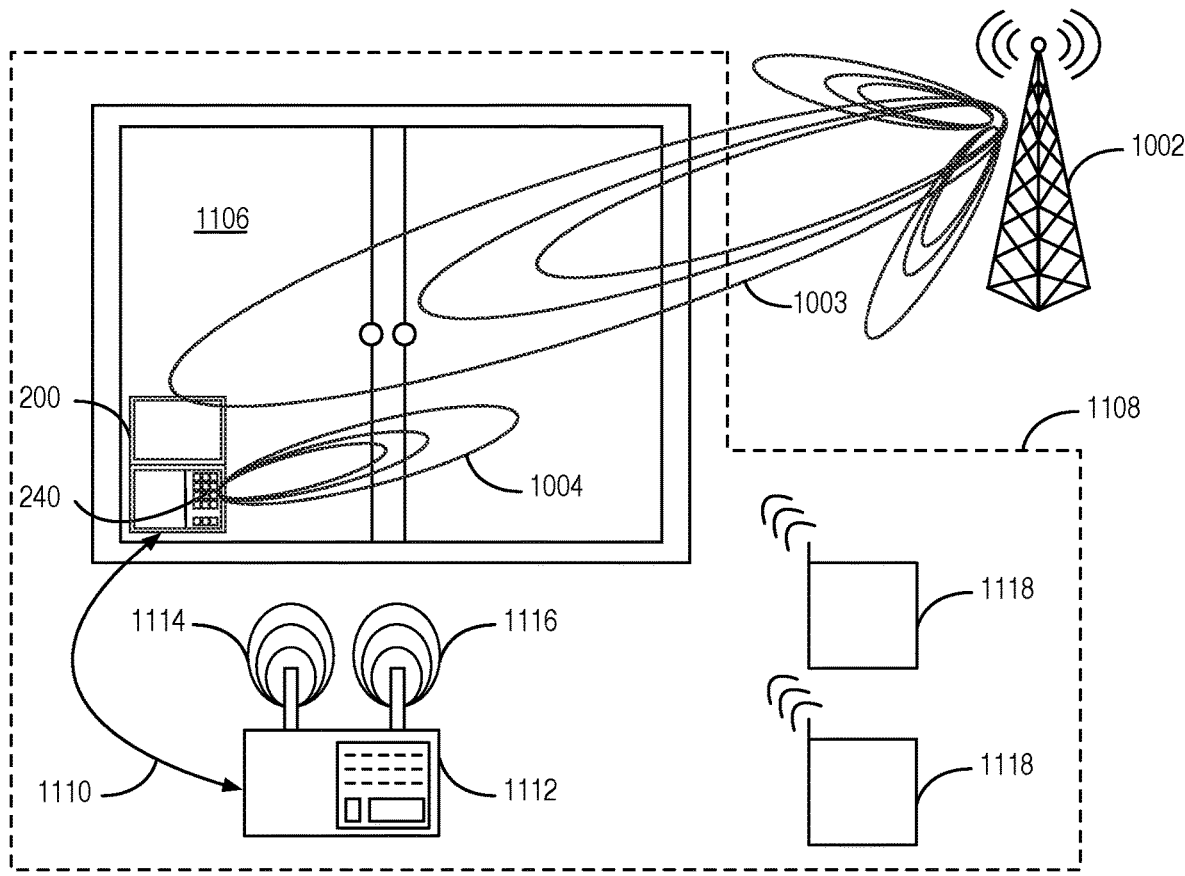
FIG. 11 illustrates an environment in which a communication tower 1002 communicates through downlink signal 1003 and uplink signal 1004 back and forth in mm wave signals between a PCCC 200 with an antenna array 240 mounted on a window 1106 inside a building 1108.

FIG. 11 shows an alternative operating environment 1100 in which a communication tower 1002 communicates through downlink signals (or beams) 1003 and 1004 back and forth in mm wave signals with a PCCC 200 (or PCCC 500) with an antenna array 240 mounted on a window 1106 inside a building 1108 (or outside the building, e.g., resting on a ledge). PCCC 200 may be mounted to window 1106 through adhesives such as suction cups or through some other type of mounting mechanisms. The mm waves 1003 sent from communication tower 1002 can be received at PCCC 200. PCCC 200 could then down convert the mm wave signals 1003 using other modules in the case 200 to lower frequency signals (e.g., approximately 2 GHz, 5 GHz, 8 GHz or the like). In some embodiments, these lower frequency signals are forwarded from a connection on the case 200 (e.g., 202*b*) through a wired coupling (e.g., a cable) 1110 to user equipment device (or a plurality of user equipment devices) 1112. PCCC 200 can also send signals wirelessly to user equipment device 1112 (e.g., using 802.11ad and/or 802.11ax). User equipment device (UED) 1112 located in the building 1108 has the ability to forward the signal through UED signals 1114 and 1116 (which typically are at different frequencies such as WiFi, Bluetooth, Zigbee, etc.) to a plurality of devices 1118 such as phones, tablets, and/or televisions. Wired coupling 1110 not only carries the RF signals received and sent to and from the antenna array 240 but it may also provide control signals and power supply for the antenna array 240. The cable 1110 can typically carry frequencies for example from approximately 0 to 8 GHz. The cable 1110 can be short or long. The UED 1112 has the processing power (i.e., CPU, baseband, modem, etc.) to handle the received signal and send signals to and from the antenna array 240. It also may contain communication modules such as WiFi radio, LTE/LTE-AILTE-U/LAA, and/or Zigbee. The UE 1112 can act as a small cell or WiFi Access Point. The UE 1112 can contact the user to the outside communication tower 1002 through the antenna array 240.

Figure 12:
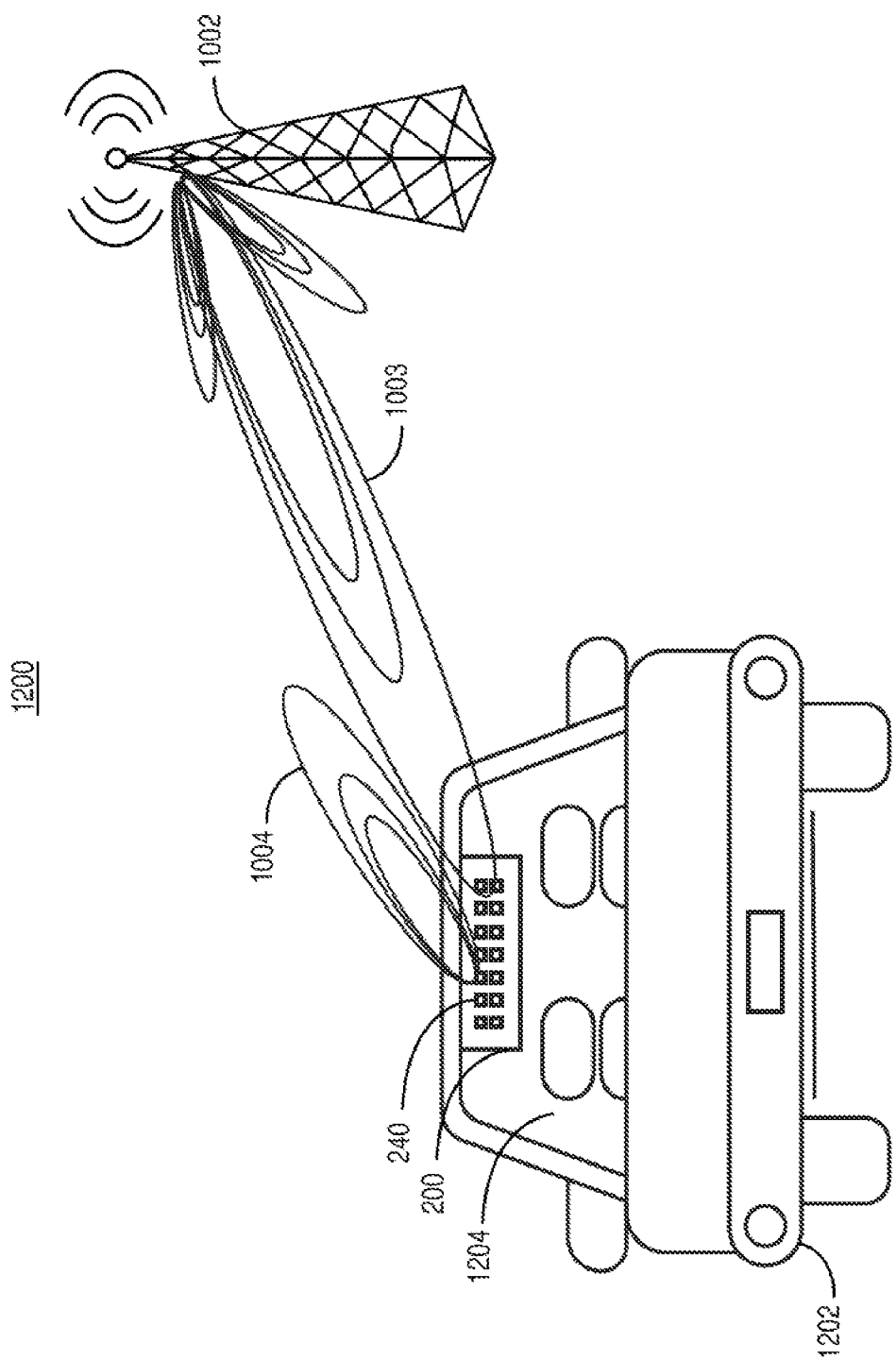
FIG. 12 shows an operating environment 1200 in which a communication tower 1002 communicates through mm wave signals 1103 and 1104 back and forth to and from a PCCC 200 with an antenna array 240 mounted in a vehicle 1202 on the glass 1204 through an adhesive.

FIG. 12 shows an alternative operating environment 1200 in which a communication tower 1002 communicates through mm wave signals 1003 and 1004 back and forth with a PCCC 200 (or PCCC 500) with an antenna array 240 mounted in a vehicle 1202 on the glass 1204 through an adhesive such as suction cups. Alternatively, the glass 1204 could be manufactured with the components of the PCCC 200 (or PCCC 500) built in.

Figure 13A:
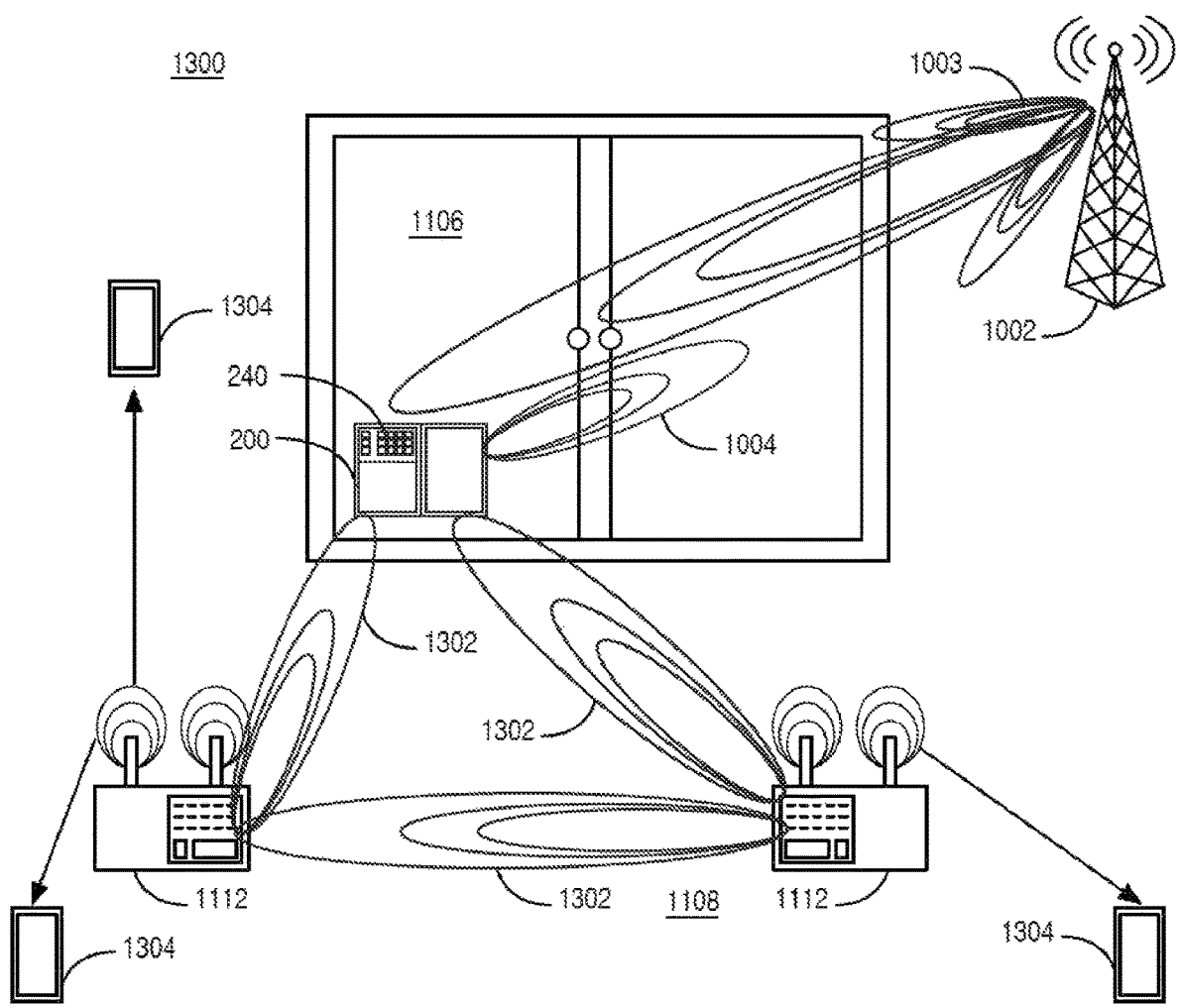
FIG. 13A shows an operating environment 1300 in which user equipment device 1112 has a PCCC 200 (e.g., mounted or integrated) so that PCCCs 200 can communicate with each other wirelessly using mm waves 1302
Figure 13B:
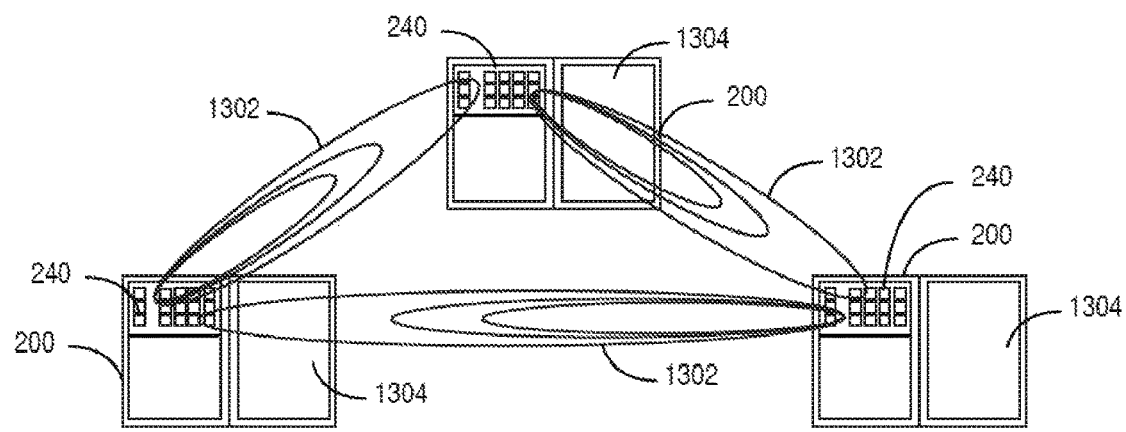
FIG. 13B illustrates a phone 1304 physically connected with a PCCC 200 (e.g., mounted or integrated) so that two PCCCs 200 can communicate with each other wirelessly.

FIG. 13A shows an alternative operating environment 1300 in which user equipment 1112 can further have a PCCC 200 mounted or integrated so that PCCCs 200 (or 500) (in this case 3 PCCCs) can communicate with each other wirelessly using mm waves 1302. A first PCCC 200 could communicate with a plurality of PCCCs 200 at the same time or different times using beam forming, multiple input/multiple output (MIMO), massive MIMO, or the like. UED 1112 can then turn the mm waves 1302 in order to wirelessly communicate with mobile communication devices such as phones, tablets, etc. 1304. In FIG. 13B a phone 1304 can have a PCCC 200 (or 500) connected (e.g., mounted or integrated), so that 2 PCCCs 200 could communicate with each other wirelessly for device to device communication. One PCCC 200 could communicate with a plurality of PCCCs 200 at the same time or different times using mm waves 1302 with beam forming, MIMO, massive MIMO, or the like.

Figure 14A:
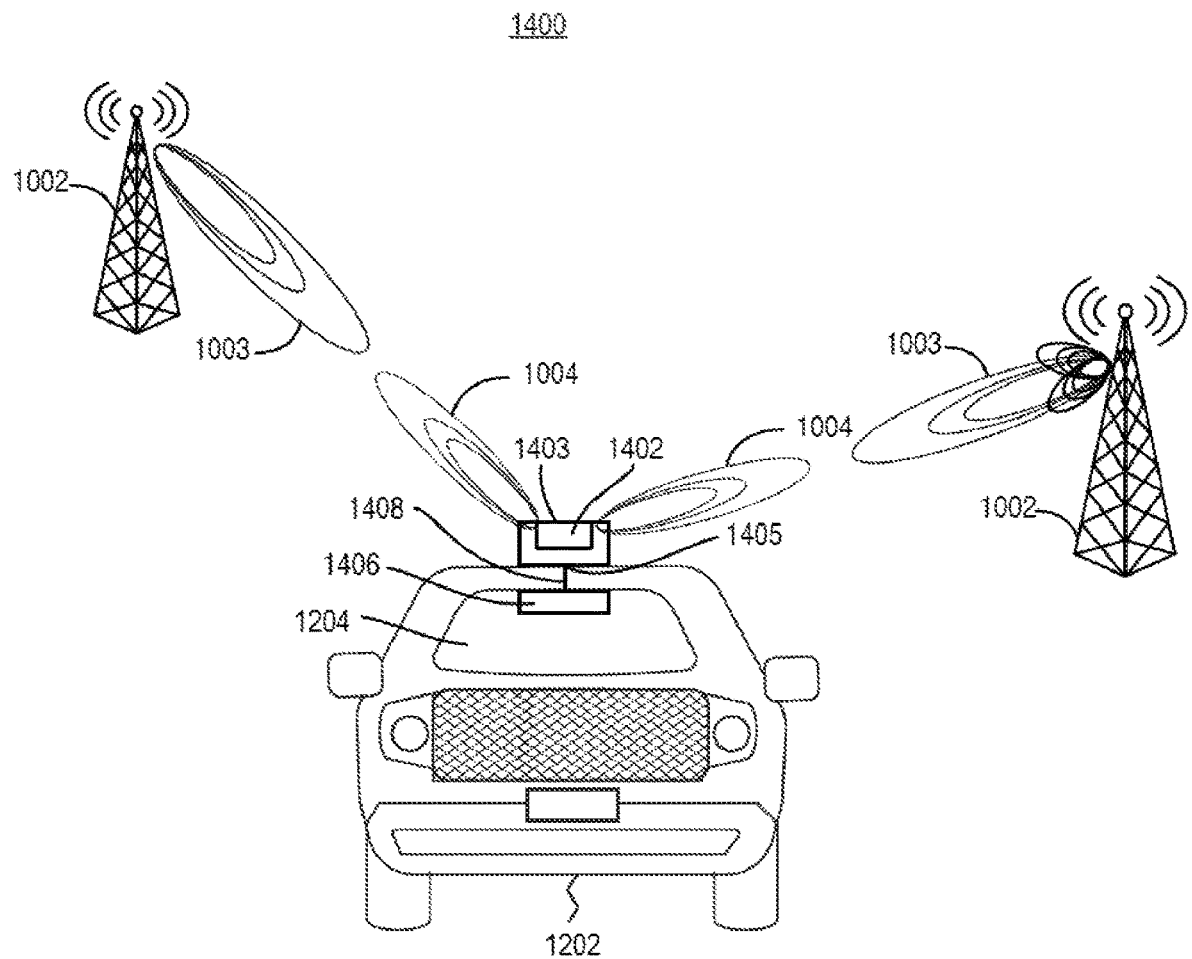
FIG. 14A shows an alternative operating environment 1400 in which a communication tower 1002 communicates through mm wave signals 1003 and 1004 back and forth with an antenna array 1402 mounted on an antenna panel 1403.

FIG. 14A shows an alternative operating environment 1400 in which a communication tower 1002 communicates through microwave and mm wave signals 1003 and 1004 back and forth with an antenna array elements (or "array" or "antenna array") 1402 mounted on antenna panel 1403. The array 1402 provides a personal cloud to the user and access to a wireless network (such as 3G, 4G, 5G, WiFi, SuperWifi, and similar technologies). As discussed above, new wireless and fixed standards keep pushing the operating frequencies into the microwave and millimeter (mm) wave spectrum (e.g., 28 GHz, 40 GHz, 60 GHz, 70 GHz, 100 GHz) and it becomes harder and harder (due to higher penetration loss and path loss) to get the signal inside buildings, houses, vehicles 102, and even mobile phones. The disclosed embodiments described herein help to make microwave and mm wave signal penetration possible. Antenna array 1402 can be a low cost antenna array made up of cells (or elements) in an N×N array (e.g. 2×2, 2×2, 4×4, 8×8, or the like) or an M×N array (e.g., 1×4, 2×4, 2×5, 2×8, or the like). The array 1402 and antenna panel 1403 could be circuit boards, the could be a chip antenna on the circuit boards, or they could be a multilayer antenna on the circuit boards. The antenna array 1402 can be used to increase the gain of the signal 1004, can be used for beam forming and beam steering, phase shifting, and/or gesture tracking. The antenna array 1402 may be coupled to and controlled by user equipment (UE) 1406 (such as a mobile communication device) wirelessly, through physical contact or through a connector (e.g., cable or electrical link(s)) 1408 running through the outer surface of vehicle 1202 (including through glass 1204).

Antenna array 1402 and antenna array panel 1403 may be configured in a plurality of ways. Antenna array 1402 may be made up of cells in an N×N or M×N array configuration as discussed above. The array panel 1403 may made of a low-cost material and a number of different substrates could be used each having their own fabrication tolerances and electrical and mechanical properties. The antenna array panel 1403 can be made of an Arion CLTE-XT (PTFE ceramic), a Rogers RT 5880/RO 3003 (PTFE glass fiber), a Rogers Liquid Crystal Polymer (LCP), a low temperature cofired ceramic (LTCC), a Parylene N dielectric, a polytetrafluoroethylene (PTFE) ceramic, a PTFE glass fiber material, a silicon material, a Gallium Arsenite (GaAs) material, an Alumina material, a Teflon material, a Duroid material or any other material that can produce thin (about 2-4 mils in thickness) metallized layers. In one embodiment, the layers may be stacked to form a multi-layer array architecture. With the antenna array 1402 printed on a thin film material, microwave and mm wave signals can penetrate through any object efficiently and at low cost.

In operating environment 1400, antenna array 1402 allows user equipment 1406 to communicate with communication towers (e.g., cell tower, base station or the like) 1002. Communication towers 1002 and antenna array 1402 could communicate with each other using, for example, time domain (TDD) or frequency domain signals (FDD). Downlink signal (or beam) 1003 coming from communication tower 1002 and uplink signal (or beam) 1004 coming from array 1402 are formed and steered to allow microwave and mm wave signal communications between the array 1402 and communication towers 1002. The antenna array 1402 may be located by communication towers 1002 using Global Positioning Satellite (GPS) technology or by 3G/4G/5G technology. Beams 1003 and 1004 may operate in the range of approximately 3 GigaHertz (GHz) to approximately 100 GHz or even higher. Typically, beams 1003 and 1004 will operate approximately in a range of plus or minus (+/−) 12% of mm wave frequency signals such as 24 GHz, 28 GHz, 39 GHz, 60 GHz, and/or 77 GHz (e.g., for 24 GHz the signal would range from approximately 21.12 GHz to approximately 26.88 GHz). Alternatively, mm wave beams 1003 and 1004 can operate in the following ranges: approximately 3.3 GHz to approximately 3.4 GHz; approximately 3.4 GHz to approximately 3.6 GHz; approximately 3.6 GHz to approximately 3.8 GHz; approximately 5.150 GHz to approximately 5.925 GHz; approximately 24.25 GHz to approximately 27.5 GHz; approximately 31.8 GHz to approximately 33.4 GHz; approximately 37.0 GHz to approximately 40.5 GHz; approximately 40.5 GHz to approximately 42.5 GHz; approximately 42.5 GHz to approximately 43.5 GHz; approximately 45.5 GHz to approximately 47 GHz; approximately 47.0 GHz to approximately 47.2 GHz; approximately 47.2 GHz to approximately 50.2 GHz; and approximately 50.4 GHz to approximately 52.8 GHz.

Antenna array 1402 may be located at any point on the vehicle 1202 including the glass 1204 (and may be printed into or attached by suction cups to the glass 1204 in an alternative embodiments). The mm waves 1003 sent from the communication towers 1002 can be received at antenna array 1402 and then down converted in communication device 1406 to lower frequency signals (e.g., approximately 2 GHz, 5 GHz, 8 GHz or the like). In some embodiments, these lower frequency signals are forwarded from array 1402 through connector 1408 which goes through the outer layer of the vehicle 1202 to the user equipment device (or a plurality of user equipment devices) 1406. The antenna array 1402 can also send signals wirelessly to user equipment device 1406 (e.g., using 802.11ad and/or 802.11ax). User equipment device 1406 located in the vehicle 1202 has the ability to forward the signal through wireless signals (which typically are at different frequencies such as WiFi, Bluetooth, Zigbee, etc.) to a plurality of devices such as phones, tablets, and/or televisions which may be located in the vehicle 1202. Wired connector 1408 not only carries the RF signals received and sent to and from the antenna array 1402 but it may also provide control signals and power supply for the antenna array 1402. The connector 1408 can typically carry frequencies for example from approximately 0 to 8 GHz. The cable 1408 can be short or long. The UE 1406 has the processing power (i.e., CPU, baseband, modem, etc.) to handle the received signal and send signals to and from the antenna array 1402. It also may contain communication modules such as WiFi radio, LTE/LTE-A1LTE-U/LAA, and/or Zigbee. The UE 1406 can act as a small cell or WiFi Access Point. The UE 1406 can contact the operator of the vehicle 1202 to the outside communication towers 1002 through the antenna array 1402.

Figure 14B:
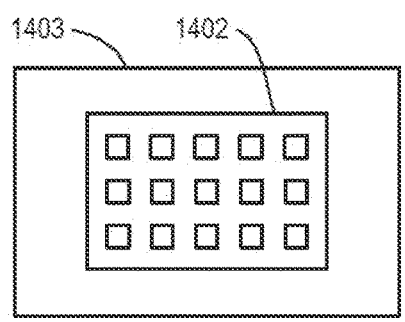
FIG. 14B is a planar view of one embodiment of the antenna array 1402 mounted on an antenna panel 1403.
Figure 14C:
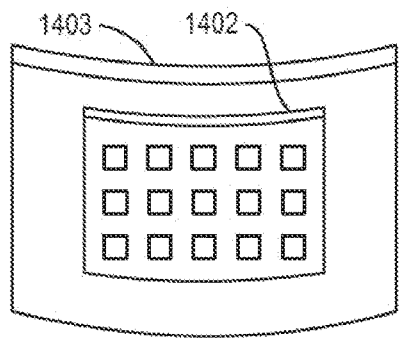
FIG. 14C is top view of an alternative embodiment of FIG. 14B in which the antenna panel 1403 and antenna array 1402 is bendable.
Figure 14D:
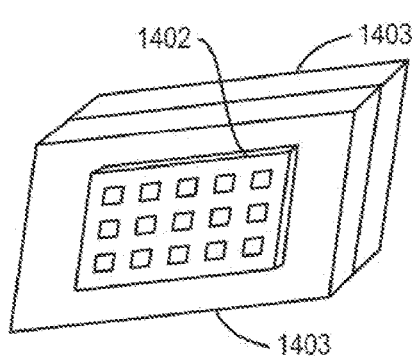
FIG. 14D is a perspective view and FIG. 14E a top view of two antenna arrays 1402 mounted on panels 1403 arranged in a back to back configuration.
Figure 14E:
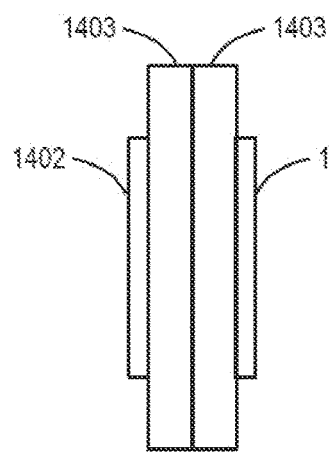
FIG. 14F is top view of an alternative embodiment of FIGS. 14D and 14E in which the antenna panels 1403 and antenna arrays 1402 are bendable.
FIG. 14G is a perspective view and FIG. 14H is a top view of three antenna arrays 1402 mounted on the exterior side of corresponding panels 1403 and arranged in a triangular configuration to improve the 360 degree reception.
FIG. 14I is a perspective view of four antenna arrays 1402 mounted on the exterior side of four panels 1403 to also improve the 360 degree reception.
FIG. 14J is a perspective view of six antenna arrays 1402 mounted on the exterior sides of panels 1403.
FIG. 14K shows a perspective view and FIG. 14L a top view of a circular antenna array 1402 mounted on the exterior of circular antenna panel 1403 to obtain 360 degree coverage.
FIG. 14M is a side view and FIG. 14N is a top view of a dome shaped antenna panel 1403 with an antenna array 1402 on top to obtain 360 degree coverage.
Figure 14F:
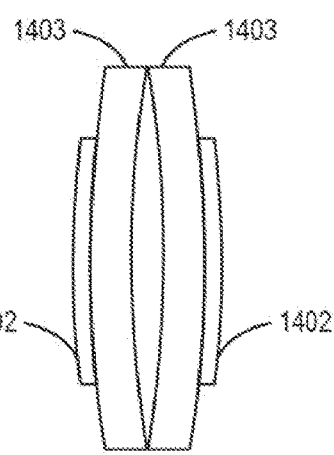
Figure 14G:
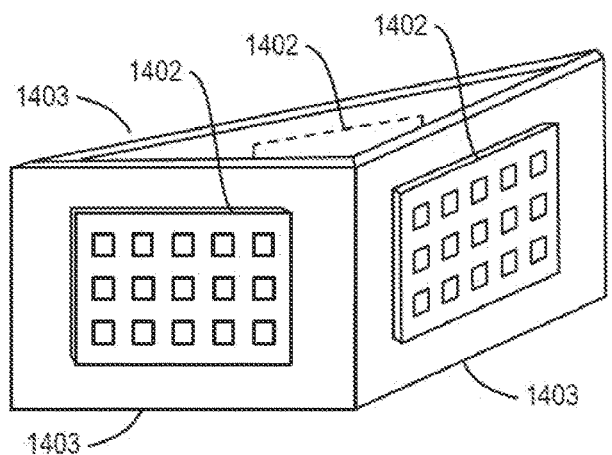
Figure 14H:
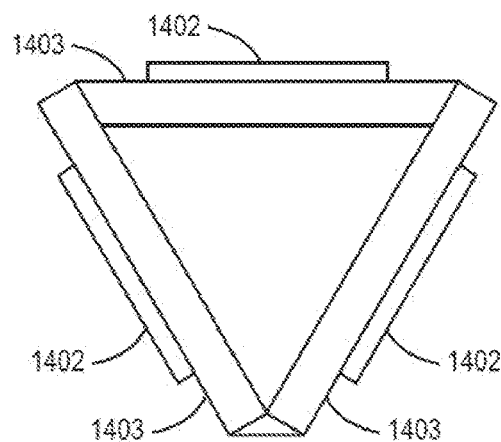
Figure 14I:
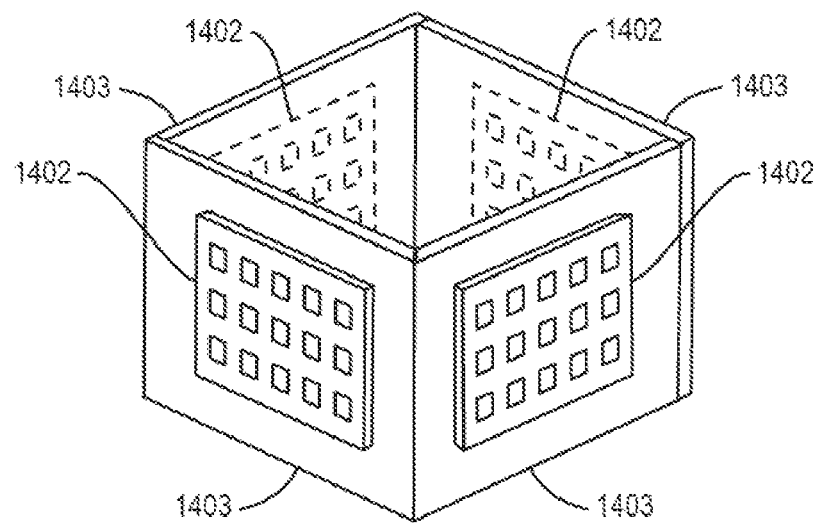
Figure 14J:
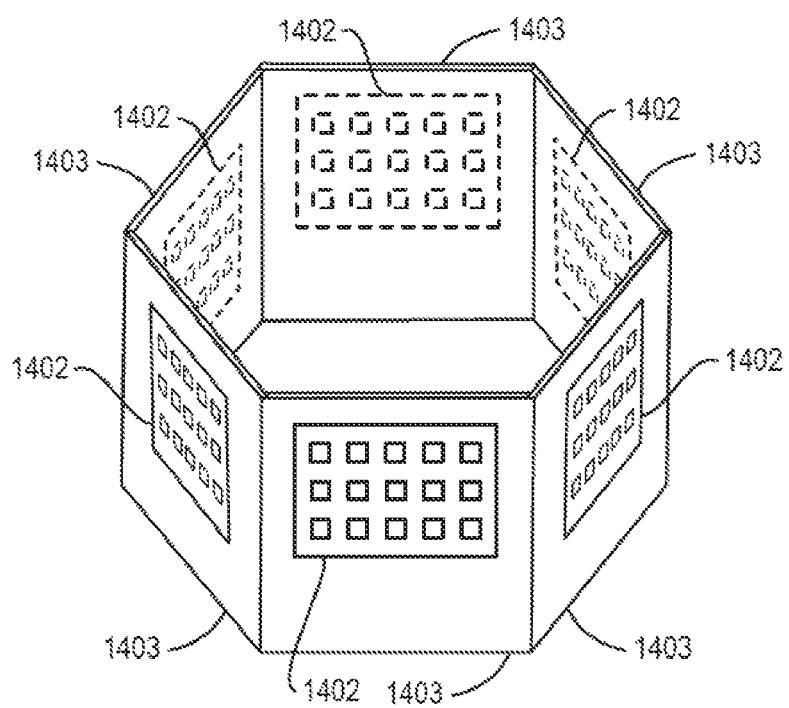
Figure 14K:
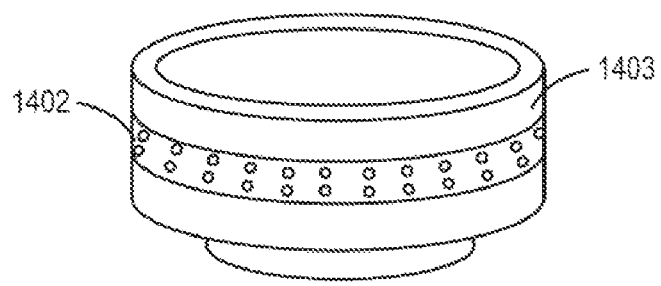
Figure 14L:
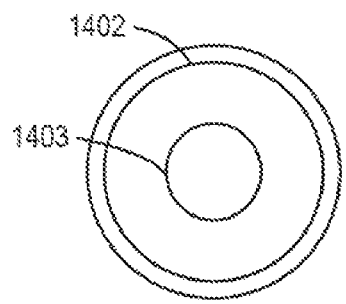
Figure 14M:
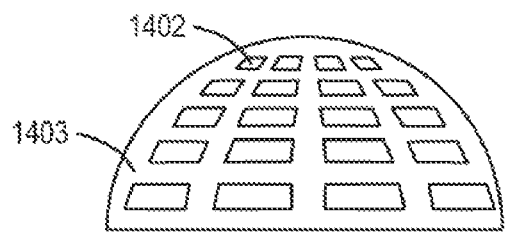
Figure 14N:
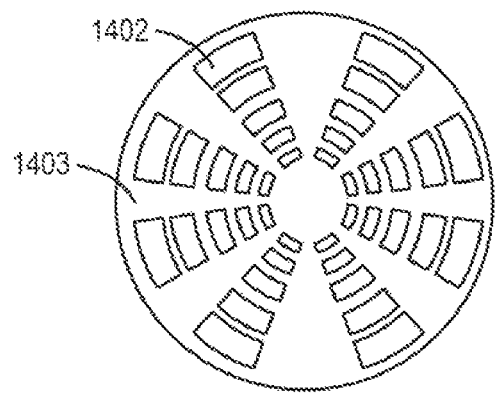

In one embodiment, antenna array 1402 may be a single array mounted on an antenna panel 1403 (e.g., a flat panel) at a platform 1405 on top of a vehicle 1202 (or any other exterior portion of the vehicle including glass 1204). In alternative embodiments, platform 1405 may have a plurality of arrays 1402 mounted on a plurality of panels 1403. The panels 1403 may be arranged in a vertical (or upright) manner compared to the platform 1405. The panels 1403 may be adjusted mechanically (or manually) or electronically to improve coverage. Coverage being the ability of the array 1402 to transmit and/or receive signals. The mechanical adjustment of panels 1403 may also depend on the phase of the arrays 1402 and the gain of the arrays 1402. Depending on the positioning of the panels 1403 to each other, coverage may extend in a range from greater than 0 degrees to 360 degrees. The term "surrounding" as used in herein means the coverage for the panels 1403 is greater than 180 degrees and up to and including 360 degrees. FIG. 14B is a planar view of one embodiment of the antenna array 1402 mounted on an antenna panel 1403. FIG. 14C is top view of an alternative embodiment of FIG. 14B in which the antenna panel 1403 and antenna array 1402 are bendable. In this case, the antenna panel 1403 may be made of a plastic material. FIG. 14D is a perspective view and FIG. 14E a top view of two antenna arrays 1402 mounted on panels 1403 arranged in a back to back configuration. This configuration allows for 360 degree transmission and reception of signals in the horizontal plane to and from tower 1002 (having a base station) and/or other cell towers. Each of the arrays 1402 is coupled to the communication device 1406. FIG. 14F is top view of an alternative embodiment of FIGS. 14D and 14E in which the antenna panels 1403 and antenna arrays 1402 are bendable. FIG. 14G is a perspective view and FIG. 14H is a top view of three antenna arrays 1402 mounted on the exterior side of corresponding panels 1403 and arranged in a triangular configuration to improve the 360 degree transmission and reception of signals in the horizontal plane. Each of the arrays 1402 is coupled to the communication device 1406. The arrays 1402 and panels 1403 may be configured in any polygonal shape such as the triangle, quadrilateral, pentagon, hexagon including up to and beyond decagons. FIG. 14I is a perspective view of four antenna arrays 1402 mounted on the exterior side of four panels 1403 to form a quadrilateral configuration with internal angles of 90 degrees (or approximately 90 degrees) and to improve the 360 degree transmission and reception of signals in the horizontal plane. Each of the arrays 1402 is coupled to the communication device 1406. FIG. 14J is a perspective view of six antenna arrays 1402 mounted on the exterior sides of panels 1403 to form a hexagon configuration. Each of the arrays 1402 is coupled to the communication device 1406. FIG. 14K shows a perspective view and FIG. 14L a top view of a circular antenna array 1402 mounted on the exterior of circular panel 1403 to obtain 360 degree coverage transmission and reception of signals in the horizontal plane. The circular configuration of array 1402 is attached to communication device 1406. FIG. 14M is a side view and FIG. 14N is a top view of a dome shaped antenna panel 1403 with an antenna array 1402 on top to obtain 360 degree transmission and reception signal coverage in the horizontal plane.

Figure 15A:
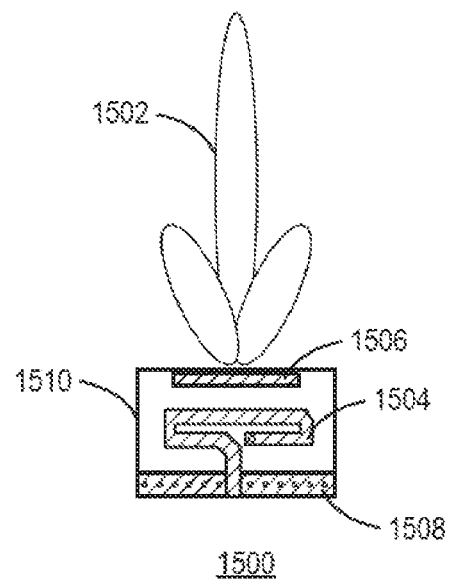
FIG. 15A shows an edge-emitting antenna (EEA) element 1500 for emitting electromagnetic waves 1502.

FIG. 15A shows an edge-emitting antenna (EEA) element 1500 for emitting electromagnetic waves 1502. The EEA element 1500 comprises a resonator 1504, one of more directors 1506, and a reflector 1508. The EEA 1500 may be constructed as metal on an antenna panel (e.g., PCB having dielectric layers) 1510 or as metal on a semiconductor die.

Figure 15B:
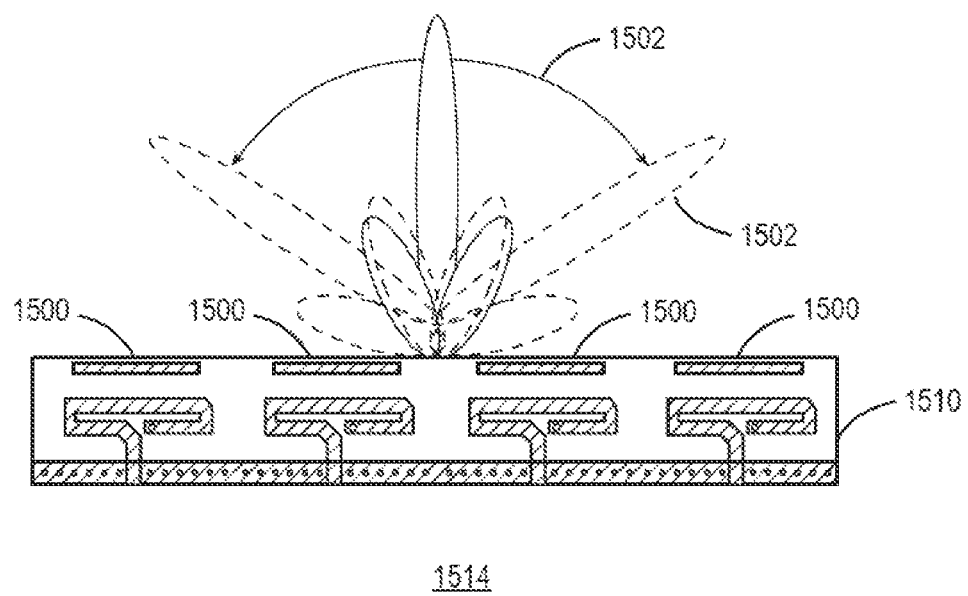
FIG. 15B shows an array 1514 of EEA's 1500 that can be used to enhance 1503 the strength of the electromagnetic wave 1502 transmitted in a selected direction.

FIG. 15B shows an array 1514 of EEA's 1500 on antenna panel 1510 that can be used to enhance the strength of the electromagnetic wave transmitted in a selected direction. The main radiating direction and pattern and the electromagnetic waves 1502 of an EEA array 1514 can be dynamically changed by changing the relative phases of RF signals being sent to the EEA elements 1500.

Figure 15C:
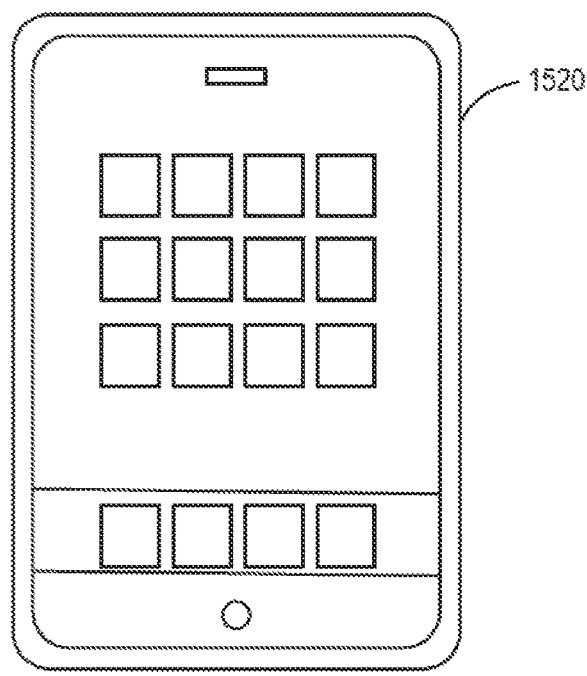
FIGS. 15C and 15D show arrays 1514 can be mounted at the edges or corners of a mobile device 1520 having a PCB 1522 such as smartphones, wireless tablets, and computers.
Figure 15D:
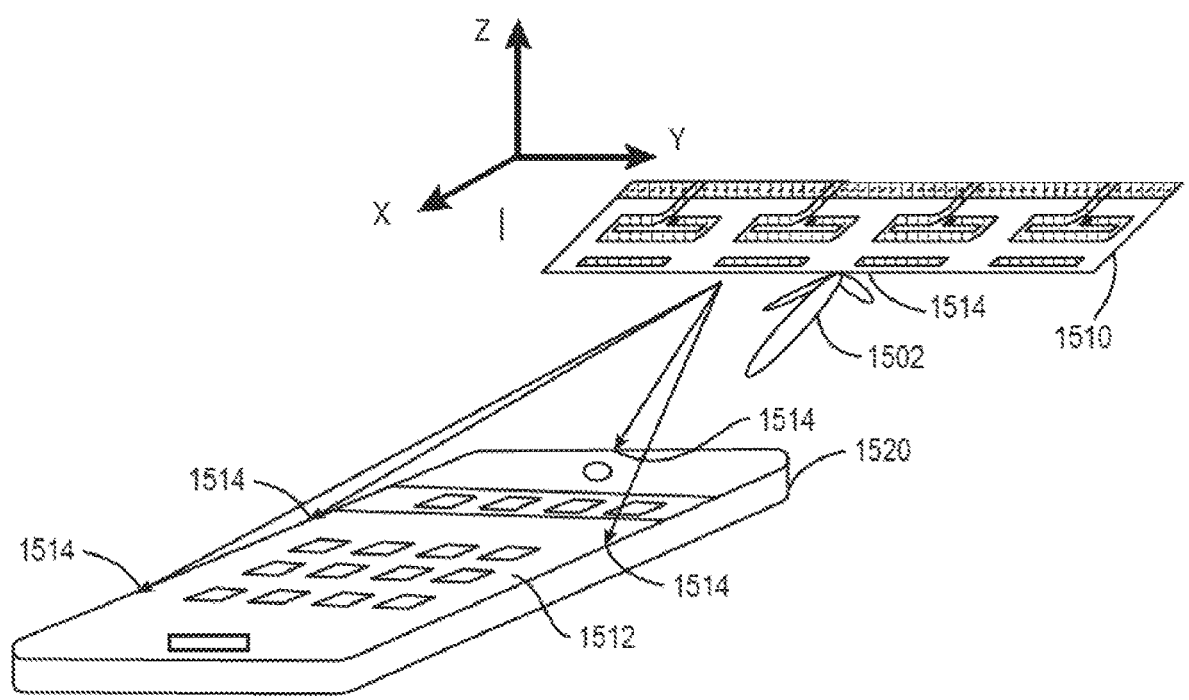

FIGS. 15C and 15D show arrays 1514 can be mounted at the edges or corners of a mobile device 1520 having a PCB 1522 such as smartphones, wireless tablets, and computers. FIG. 15D is a perspective view showing electromagnetic waves 1502 of EEA array 1514 emitting radio frequency signals (e.g, microwave and mmWave signals) primarily on horizontal (X-Y) plane of the antenna panel 1510 or the semiconductor die. As shown in FIG. 15D, EEA array 1514 is mounted in the X-Y plane parallel to the face of PCB 1522 of a mobile device 1520 and the radio waves are emitting from the edges, sides or the corners of the mobile device 1520 advantageously. The radio waves are transmitted and received substantially in the X-Y plane of the antenna panel 1510 of the array 1514 to avoid interference with other circuitry on the PCB 1522. EEA array 1514 can also be used to transmit RF to a preferred direction or to receive RF signals from a preferred direction, or to both transmit and receive RF signals to and from a preferred direction.

Figure 15E:
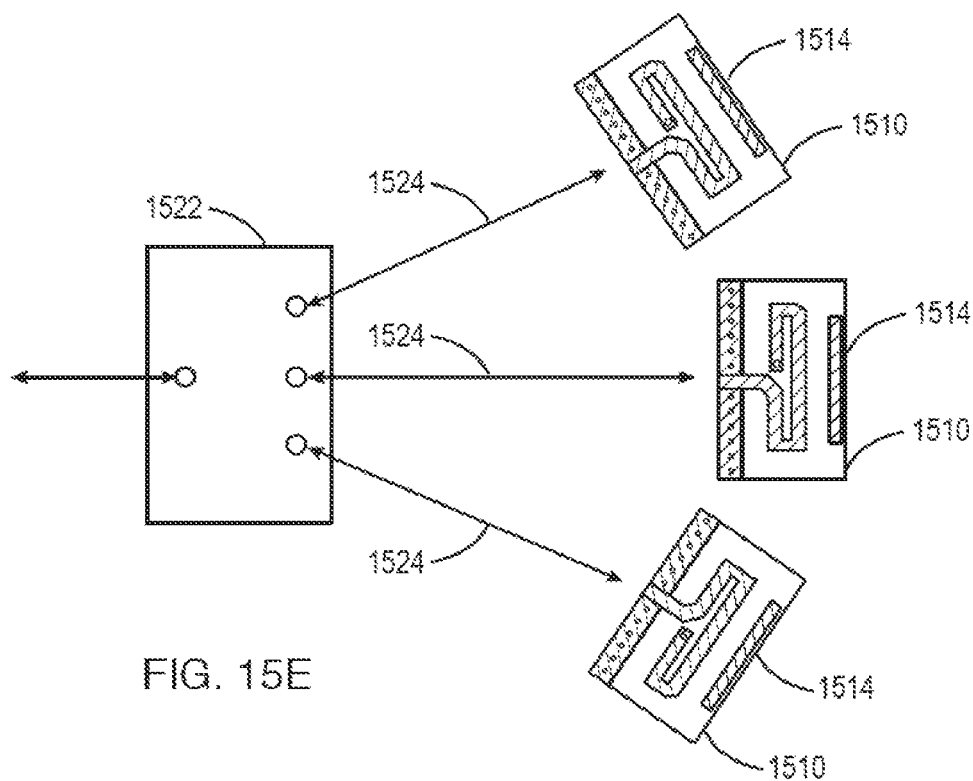
FIG. 15E shows EEA arrays 1514 (or could be individual EEA elements in an alternative embodiment) which could be arranged to have the primary radiation pointing to or from different directions.

FIG. 15E shows EEA arrays 1514 which could be arranged to have their primary radiation and reception pointing to or from different directions. FIG. 15E shows the EEAs arrays 1514 pointing, for example, in three different directions at different angles of coverage to improve the coverage range. EEA arrays 1514 can function independently or jointly and may be controlled by switch 1522 and receive and send signals through lines 1524. There can be a switch 1522 for RF signals 1524 to different EEA arrays 1514. RF switch 1522 can be used to select the antenna for a preferred direction.

Figure 15F:
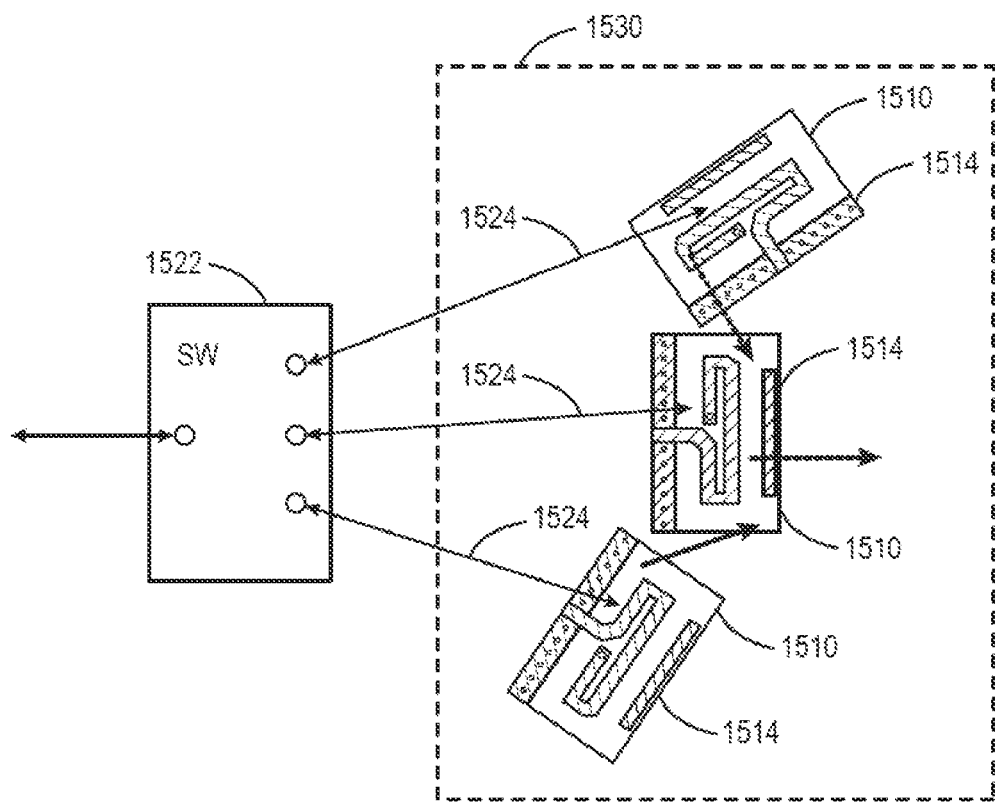
FIG. 15F shows EEA arrays 1514 (or could be individual EEA elements 1500 in an alternative embodiment) in a stack of multiple layers and be arranged to have its primary radiation pointing to or from different directions.

FIG. 15F shows EEA arrays 1514 formed in a stack of multiple layers 1530 and be arranged to have its primary radiation and reception pointing to or from different directions. EEA arrays 1514 can function independently or jointly. Each layer can be used to transmit, to receive, or both to transmit and to receive. Each layer could be combined to shape the electromagnetic wave beam 1502. Having EEA arrays 1514 pointing to different directions could eliminate phase shifters and complex computing. As discussed with FIG. 15E, EEA array 1514 layers can function independently or jointly and may be controlled by switch 1522 and receive and send signals through lines 1524. There can be a switch 1522 for RF signals 1524 to different EEA arrays 1514. RF switch 1522 can be used to select the antenna for a preferred direction.

Figure 15G:
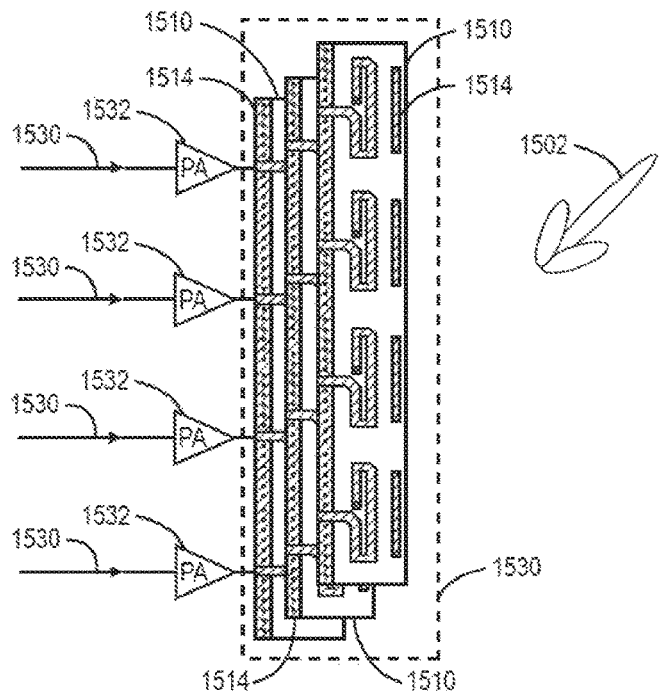
FIG. 15G shows a multi-layer antenna array 1530 made up of EEA arrays 1514 receiving signals 1530 through power amplifiers 1532 and transmitting electromagnetic wave RF signals 1502.

FIG. 15G shows a multi-layer antenna array 1530 receiving signals 1530 through power amplifiers 1532. Antenna arrays 1514 can be used for transmitting and receiving RF signals from selected directions.

Figure 15H:
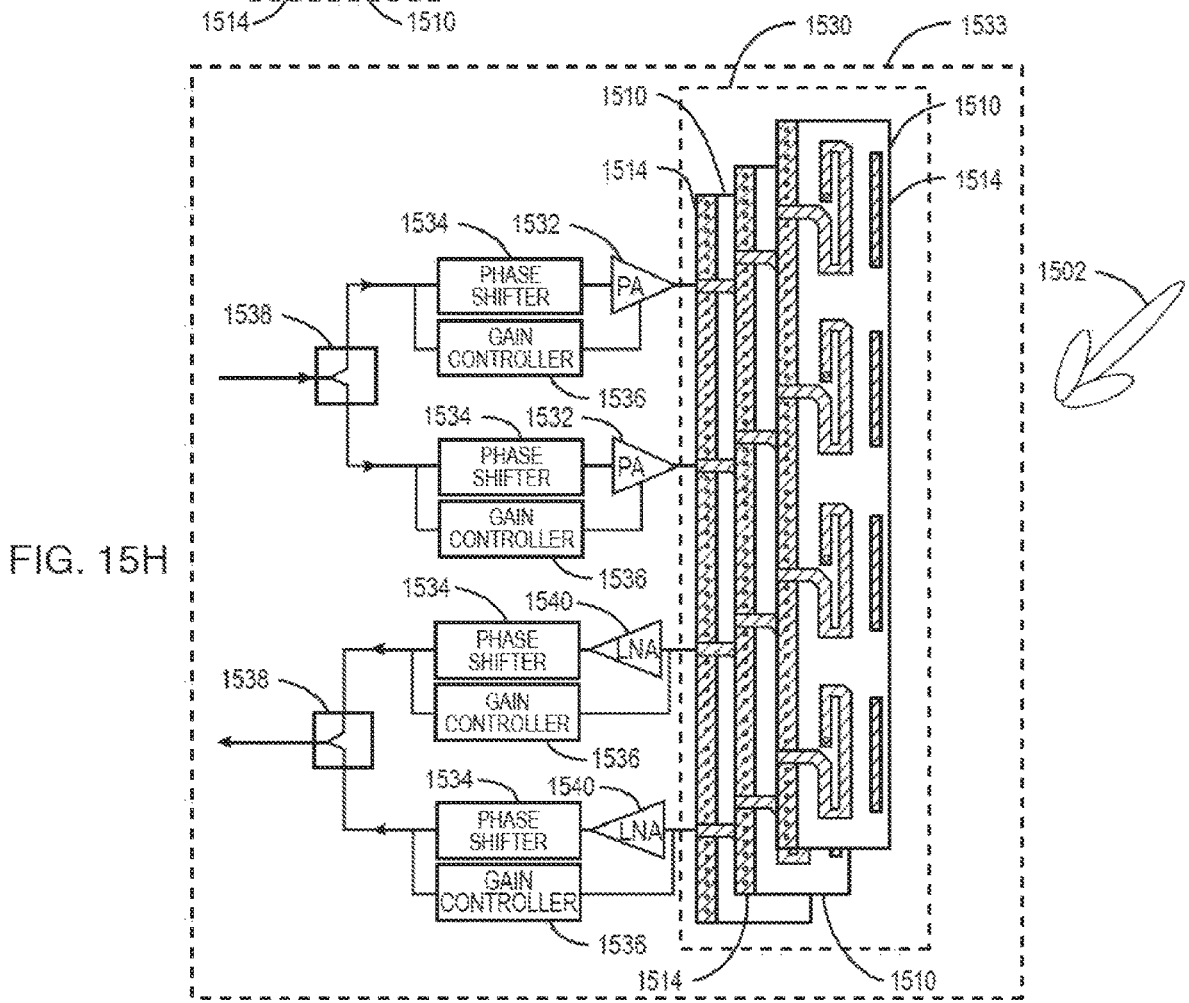
FIG. 15H shows a multi-layer antenna array 1530 made up of EEA arrays 1514 which is part of an antenna array module 1533 that can be used to transmit or to receive electromagnetic wave RF signals 1502.

FIG. 15H shows a multi-layer antenna array 1530 made up of EEA arrays 1514 which is part of an antenna array module 1533 that can be used to transmit or to receive RF signals (e.g., mmWave or microwave signals). The module 1533 includes circuitry necessary for RF communications such as power amplifiers 1532, phase shifters 1534, gain controllers 1536, splitters 1538, and low noise amplifiers 1540.

Figure 15I:
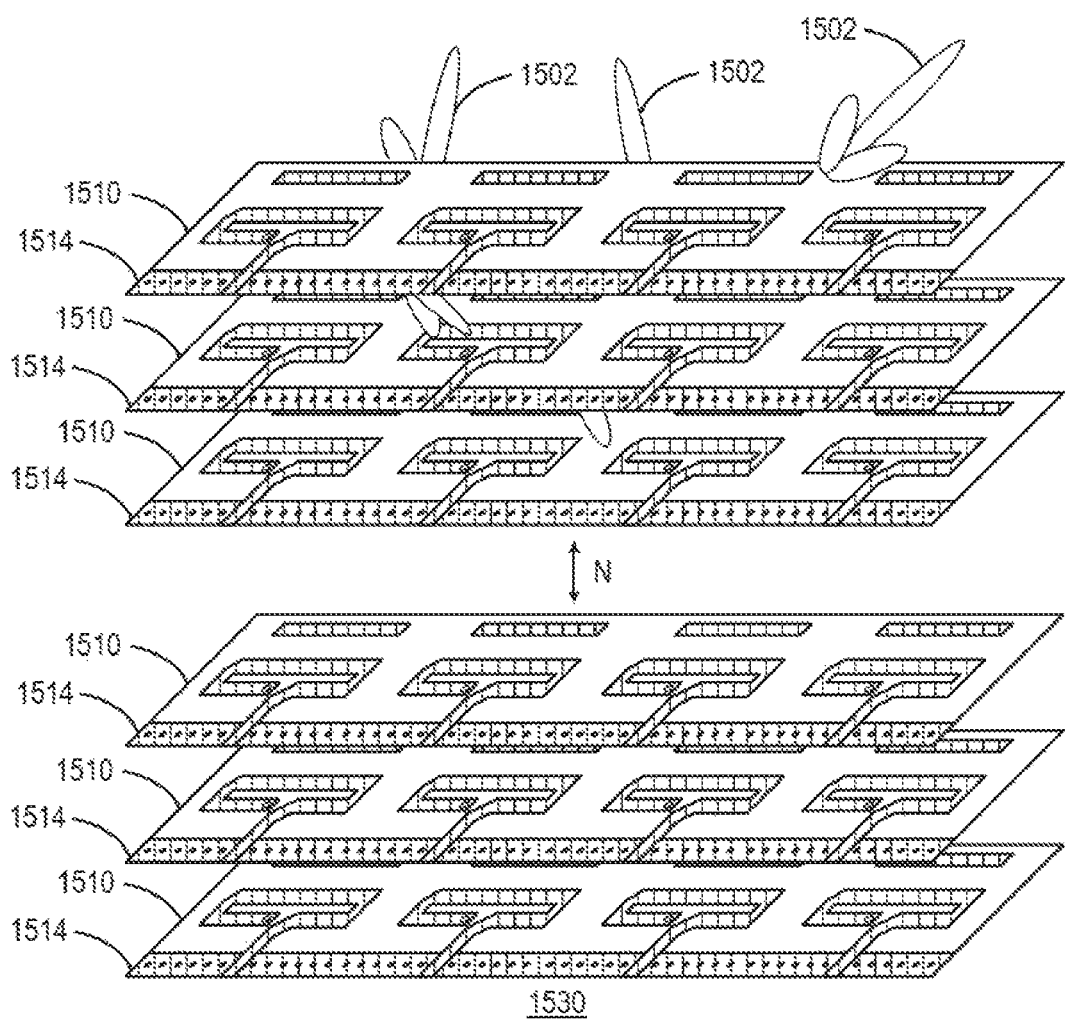
FIG. 15I shows a multilayer EEA array 1530 made up of N+1 array 1514 layers in a range of 2 to 10 or greater with each layer 1514 capable of functioning independently or jointly.

FIG. 15I shows that a multilayer EEA array 1530 could be made up of N+1 array 1514 layers in a range of 2 to 10 or greater with each layer 1514 capable of functioning independently or jointly.

Figure 15J:
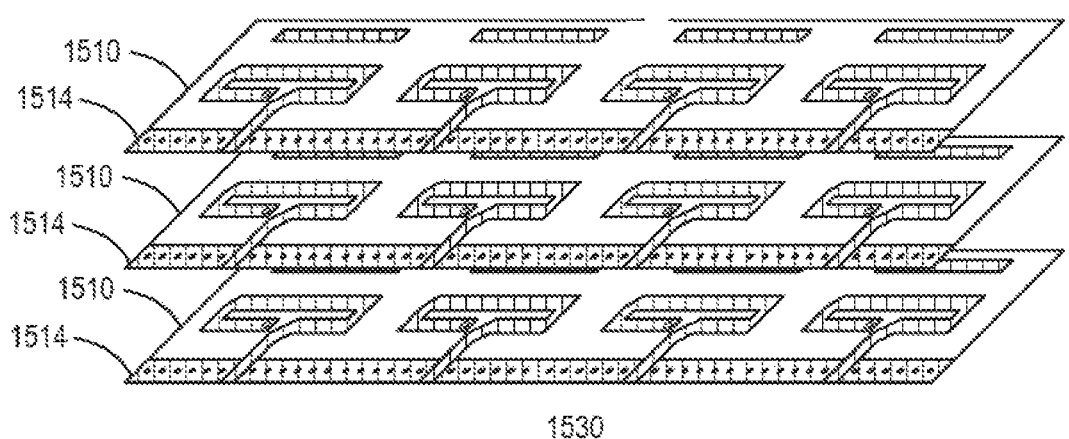
FIG. 15J shows that a multilayer EEA array 1530 could be configured so that each layer 1514 can function independently or jointly (e.g., operating at different frequencies).

FIG. 15J show that a multilayer EEA array 1530 could be configured so that each layer 1514 can function independently or jointly (e.g., at different frequencies). Each layer can be used to transmit, to receive, or both to transmit and to receive for preferred directions at different frequencies. Each layer 1514 could be combined to shape the electromagnetic beam 1502.

Figure 16:
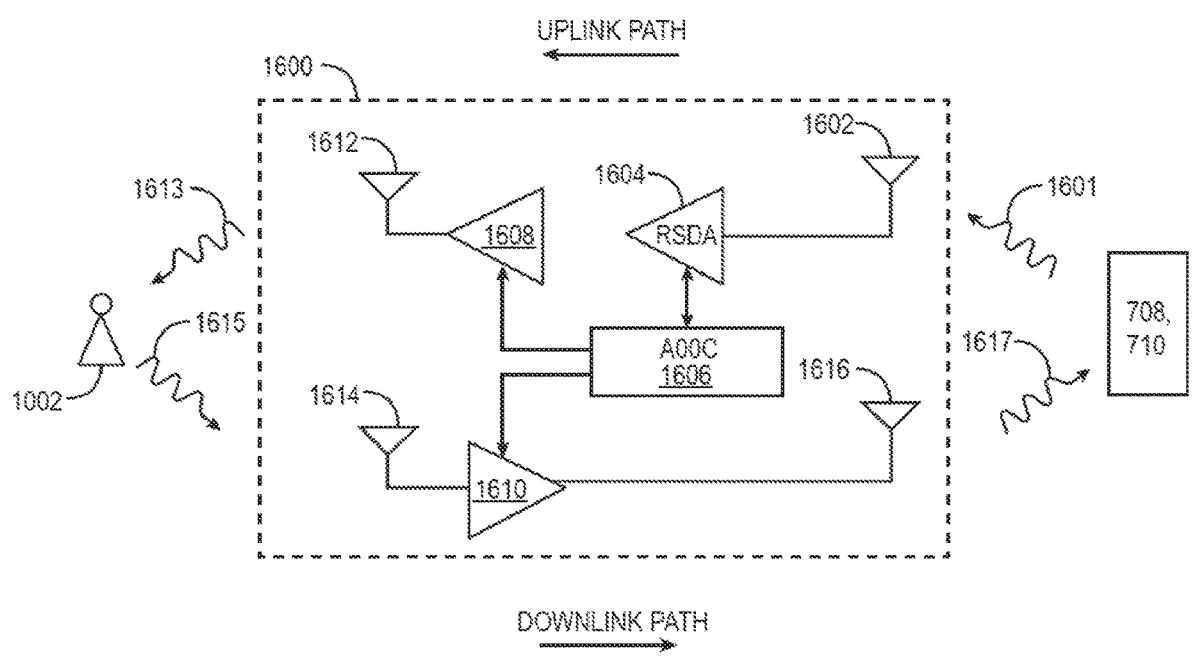
FIG. 16 shows a radio frequency (RF) front end in a device 1600 with automatic transmission/reception (Tx/Rx) function by signal detection.

FIG. 16 shows a radio frequency (RF) front end in a device (or housing) 1600. The RF front end device 1600 can communicate with both base stations (BS) 1002 and wireless user terminals (UT) 708, 710. An RF signal 1601, originated from a wireless user terminal 708, 710, traveling from antenna 1602 to antenna 1612 for transmitting to base station 1002 is an uplink (UL) signal. Conversely, an RF signal 1615, originated from a base station, traveling from antenna 1614 to antenna 1616 for transmitting to wireless user terminal 708, 710 is a downlink (DL) signal. A wireless terminal unit (e.g., user devices such as cell phones 708, personal computers or tablet computers 710, connected vehicles, and other internet of things IoT devices) is capable of sending a signal to the unit 1600 and to be received by antenna 1602. Unit 1600 is under the control of automatic on/off controller (AOOC) 1606. When there is no signal from the wireless terminal unit, the downlink path is on and the uplink path is off. In a start state (or normal state) when there is no uplink signal from the wireless terminal unit, low noise amplifier (LNA) 1610 in the downlink path is on and receive signal detector and amplifier (RSDA) 1604 and power amplifier 1608 in the uplink path are off (which will be discussed below). When antenna 1602 receives a uplink signal 1601 from the wireless terminal device it travels on the uplink path to receive signal detector and amplifier (RSDA) 1604. RSDA 1604 is a signal detector and amplifier which detects and amplifies the received signal having a first frequency. Automatic on/off controller (AOOC) 1606 based on a signal indication from the RSDA 1604 turns on the operations of power amplifier (PA) 1608 and simultaneously turns off low noise amplifier (LNA) 1610. This LNA is turned off when the power amplifier 1608 is turned on to prevent uplink path and downlink path forming a feedback loop which would result in oscillation, noise and interference. The uplink signal is subsequently amplified by power amplifier 1608 and sent to antenna 1612 which transmits an RF signal 1613 to a base station 1002. The frequency of signal 1601 and 1613 will be the same. RSDA 1604 allows RF uplink signals at antenna 1602 to be autonomously amplified without the intervention of physical layer controls such as controls from modem or digital baseband. After transmission of signal 1613, the controller 1606 resets to the normal operating state by turning LNA 1610 in the downlink path back on and the power amplifier 1608 in the uplink path off. Antenna 1614 is capable of receiving a downlink signal 1615 at a second frequency which is amplified by the turned on LNA 110. This amplified signal is sent to antenna 1616 which transmits an RF signal 1617 to the wireless terminal unit 708,710. The first and second frequencies may be the same or different.

Figure 17:
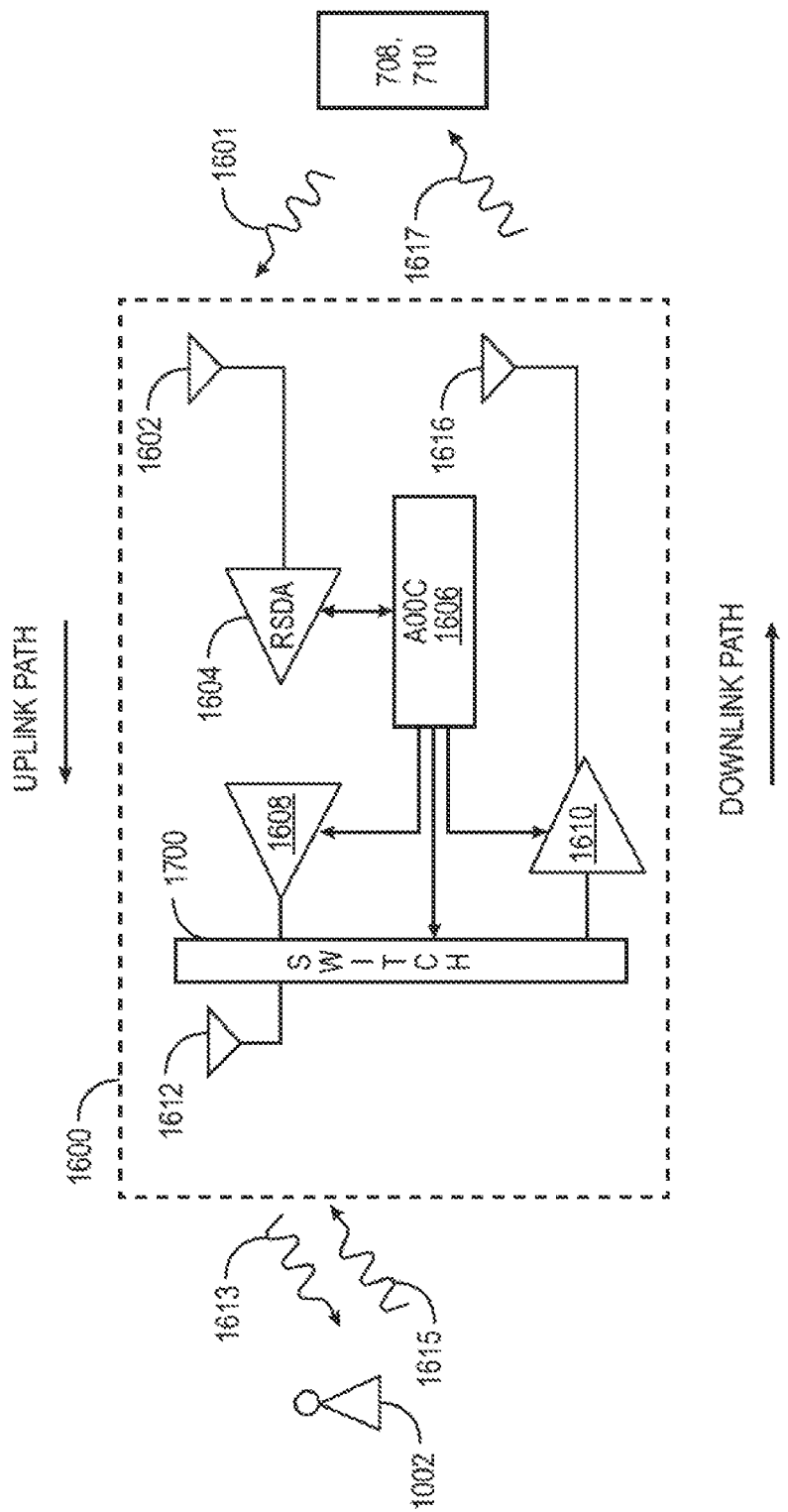
FIG. 17 shows a radio frequency (RF) front end in the device 1600 with automatic transmission/reception (Tx/Rx) function by signal detection with a switch.

FIG. 17 shows an alternative embodiment of unit 1600. In this embodiment, instead of a plurality of antennas (1612, 1614), a switch 1700 is coupled to a single antenna 1612 to connect uplink or downlink paths to the antenna 1612. Switch 1700 is also controlled by automatic on/off control (AOOC) 1606 which allows autonomous transmitting or receiving operations at antenna 1612. In a normal state, the switch 1700 allows the downlink path to be open and when a first signal is received at RSDA 1604, the AOOC 1606 changes the transmission path to the uplink path.

The RF device 1600 overcomes the complexity of conventional approaches by eliminating complicated circuit structure with up/down converters, digital to analog (D/A), digital control and the like. RF device 1600 is purely analog. In RF signal transmission, the strength of a signal drops as its travelling distance increases or from passing through barriers such as building structures, walls, or windows. But background noise level remains. As a result, the signal to noise ratio (S/N ratio) drops to a level that the signal can no longer carry the information to be communicated. RF device 1600 senses the radio waves in the air and amplifies them automatically so that the signal is strong enough compared to background noise. This allows the signal to continue to propagate with good signal noise ratio (S/N), sufficient to get through barriers and continue to propagate. Therefore RF device 1600 is simple, and can be made into compact integrated circuits with semiconductors such as gallium arsenide (GaAs), silicon germanium (SiGe), and complementary metal oxide silicon (CMOS) to be low in cost.

Figure 18:
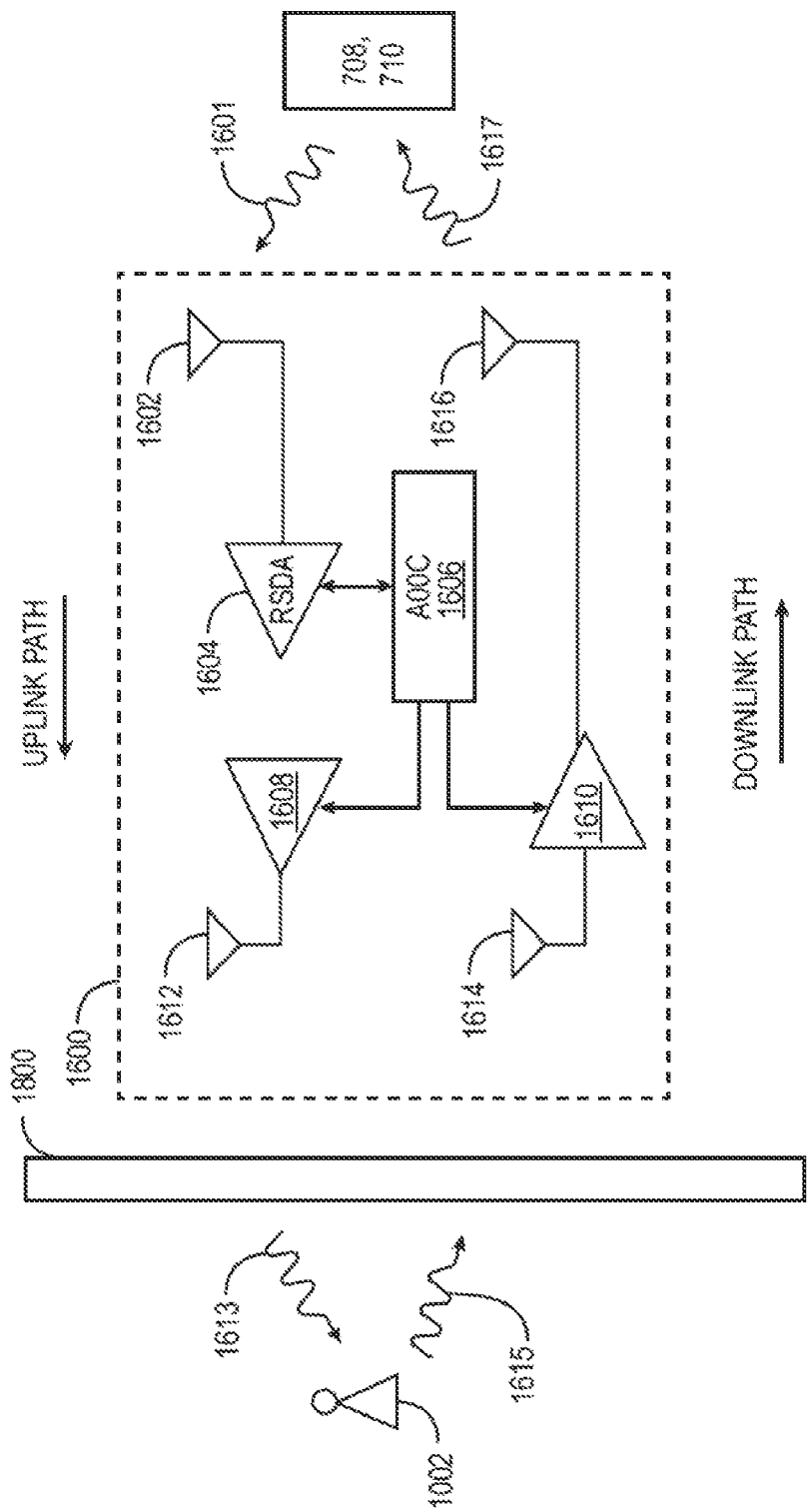
FIG. 18 shows an RF device 1600 on the other side of a barrier 1800 such as glass, a wall, or the like from a base station 1002.

FIG. 18 shows the RF device 1600 on the other side of a barrier 1800 such as glass window, a wall, or the like from the base station 1002. The barrier 1800 can diminish signals so that they are attenuated when they make through the barrier. Antenna 1614 is able to detect these faint signals and amplify them in the LNA 1610.

Figure 19:
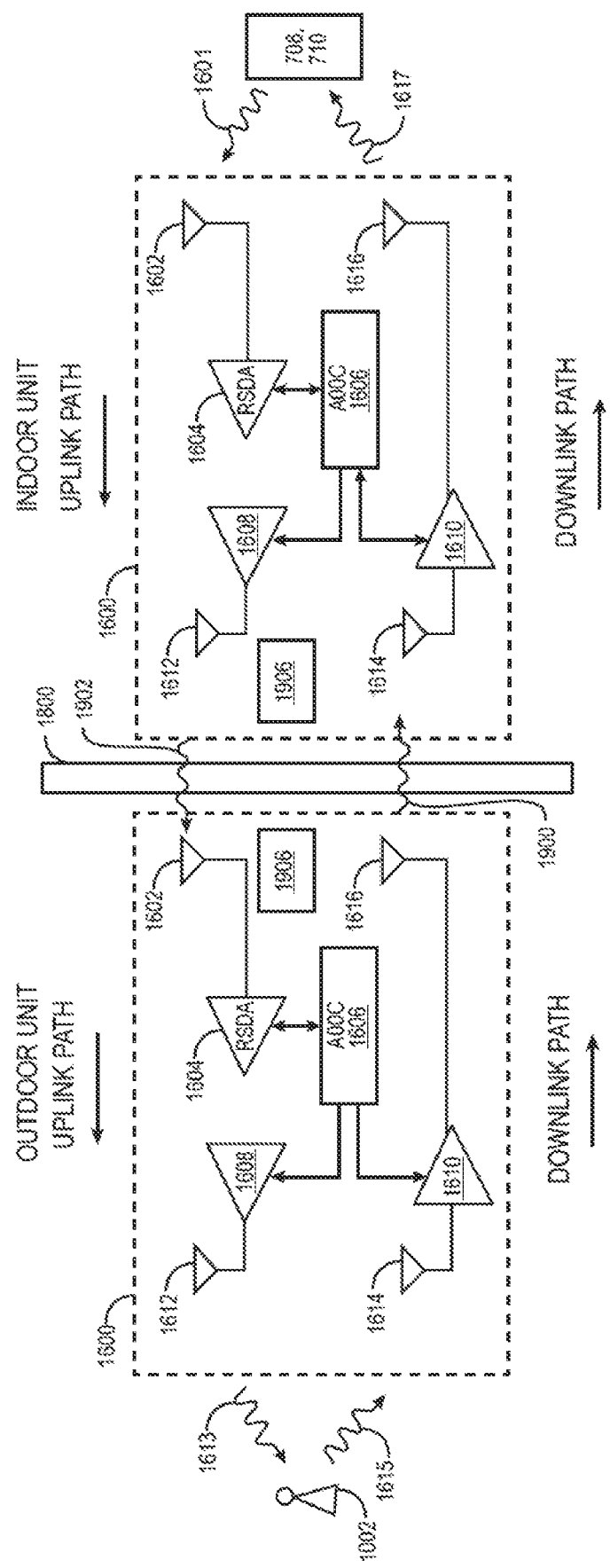
FIG. 19 shows two RF devices 1600 which are aligned on both sides of a barrier 1800.

FIG. 19 shows two RF devices 1600 operate as discuss above and which are aligned on both sides of a barrier 1800 wall or window. RF signal 1900 from the outdoor device 1600 penetrates the barrier 1800 to reach the indoor device 1600. RF signal 1902 from the indoor unit penetrates the barrier 1800 to reach the outdoor unit. Reference item 1904 indicates that each of the indoor and outdoor devices 1600 may have their orientations adjusted in three dimensions so as to align with each other. Reference 1906 indicates mechanical attachment devices such as a magnet or a physical attachment device that allows devices 1600 to be attached to the surface of the barrier 1800 or some other object.

Figure 20A:
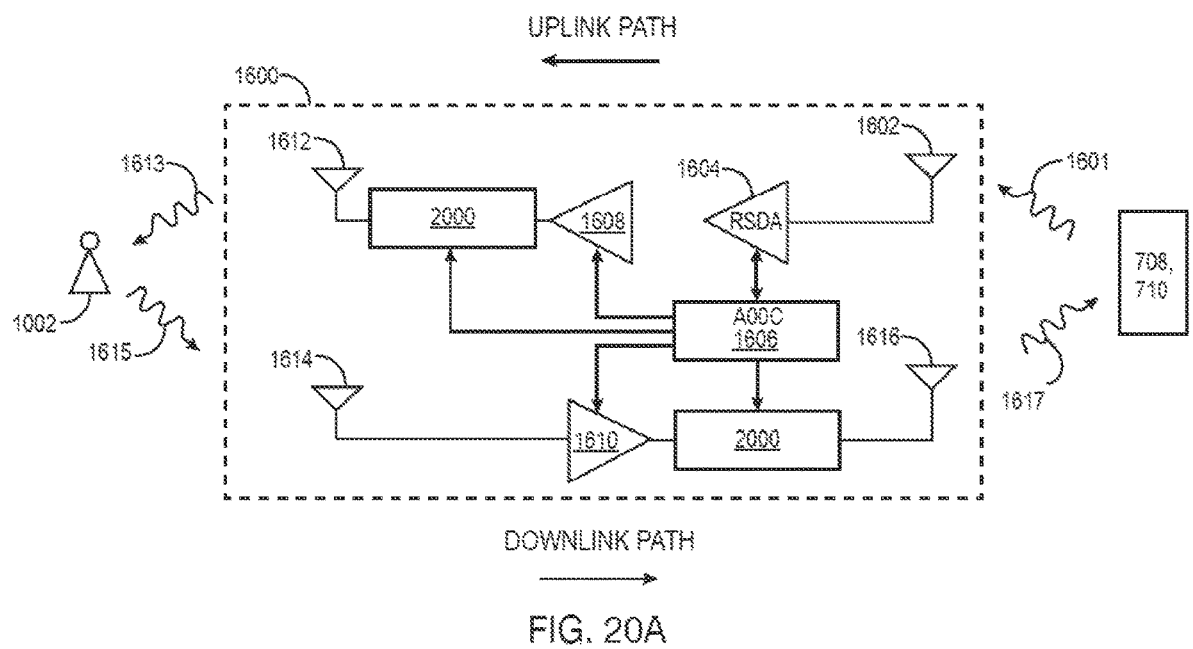
FIG. 20A shows an alternative embodiment of device 1600 in which each of the antennas 1602, 1612, 1614 and 1616 are mechanically adjustable (e.g., bendable, screw driver adjustable) so that the operator can align them with base station 1002 or wireless terminal device 708, 710.
Figure 20B:
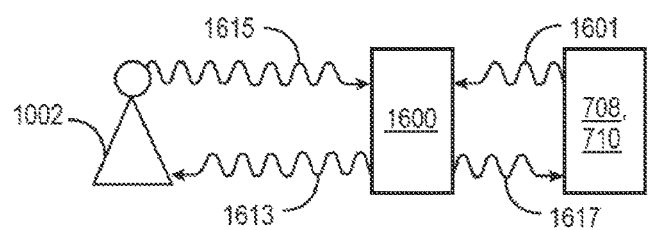
FIG. 20B shows device 1600 aligned with and receiving long distance signals from a base station and FIG. 20C shows the device 1600 positioned to align with both a base station 1002 and a wireless terminal device 708, 710 to avoid a large obstacle such as a building.
Figures 20C, 21:
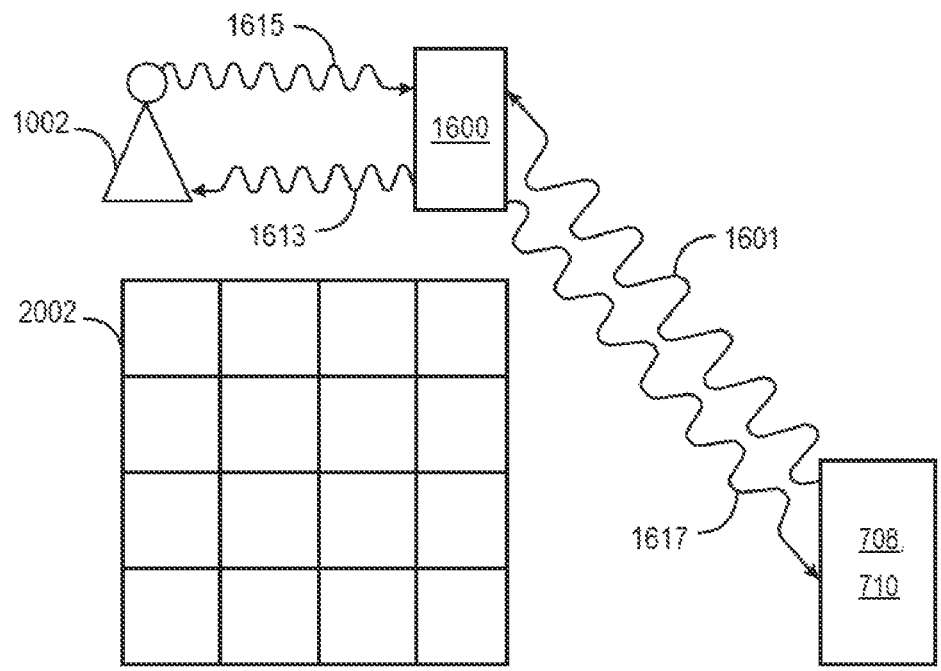
FIG. 21 shows a front view close up of antenna array 2100. Antenna array 2100 is a low cost antenna array in the form of a panel made and/or printed on a thin film material.

FIG. 20A shows an alternative embodiment of device 1600 in which each of the antennas 1602, 1612, 1614 and 1616 are mechanically adjustable (e.g., bendable, screwdriver adjustable) or electronically steerable so that the operator can align them with either or both of the base station 1002 or the wireless terminal device 708, 710. FIG. 20B illustrates that the device 1600 may able to align with the base station 1002 for long distance communications. FIG. 20C illustrates that the device 1600 may also be aligned with both the base station 1002 and wireless terminal device 708, 710 to avoid an obstacle such as a building 2002. Alternatively, antenna array with phase shifters 2000 may be included in the uplink and/or downlink paths to adjust the transmission beam to electronically steer and align with the base station 1002 and/or wireless terminal 708, 710. The ability to adjust the alignment of device 1600 allows for a line of sight that avoids obstacles such as trees, houses, large buildings and the like. In an alternative embodiment, the device 1600 may have antenna array with phase shifters 2000 in the uplink path that are controlled by the AOOC 1606 to shift the beam signal to avoid obstacles to reach the base station 1002.

Signals (or beams) 1601, 1613, 1615, 1617, 1900 and 1902 may be RF signals. In particular, these signals may operate in the range of approximately 300 Megahertz to approximately 30 GigaHertz (GHz) and/or in the mmWave range of approximately 30 GHz to approximately 300 GHz or even higher. These signals may also operate in the range of 2 GHz to 100 GHz. Typically, these signals will also often operate approximately in a range of plus or minus (+/−) 20% of mmWave frequency signals such as 24 GHz, 28 GHz, 39 GHz, 60 GHz, and/or 77 GHz (e.g., for 24 GHz the signal would range from approximately 19 GHz to approximately 29 GHz). Alternatively, the signals can operate in the following ranges: approximately 2 GHz to approximately 12 GHz, approximately 5.95 GHz to approximately 7.1 GHz; approximately 24 GHz to approximately 60 GHz.

FIG. 21 shows a front view close up of antenna array 2100. Antenna array 2100 is a low cost antenna array in the form of a panel made and/or printed on a thin film material. The device 1600 and the antennas (1602, 1612, 1614 and 1616) can be easily attached to any surfaces of a building, or fixtures attached to a building. One of the preferred arrangements is window glass which has minimal obstructing views of the base station. The antenna array 2100 can be applied and/or attached to windows, walls, smartphones, mobile phone casings, PCCCs, vehicles and the like. The antenna array 2100 is made up of a plurality of M by N (M×N) or N by N (N×N) antenna elements arranged in a matrix. The matrix of antenna elements may be 1×4, 4×4, 8×8, 12×12, and others. The antenna array 2100 can capture microwave and/or mmWave signals. The antenna array 2100 can be located inside or outside buildings, on a building wall, on a post, on a corner, and/or vehicles. Radio wave beams can be formed and steered by adjusting the phases of signals transmitted or received from the elements of the antenna array 2100. Antennas 1602, 1612, 1614 and 1616 discuss above may all be antenna arrays as described herein.

Approximately or About: refers herein to a value that is almost correct or exact. For example, "approximately" or "about" may refer to a value that is within 1 to 10 percent of the exact (or desired) value. It should be noted, however, that the actual threshold value (or tolerance) may be application dependent. For example, in some embodiments, "approximately" or "about" may mean within 0.1% of some specified or desired value, while in various other embodiments, the threshold may be, for example, 2%, 3%, 5%, and so forth, as desired or as required by the particular application.

Automatically: refers herein to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Communication: in this disclosure, devices that are described as in "communication" with each other or "coupled" to each other need not be in continuous communication with each other or in direct physical contact, unless expressly specified otherwise. On the contrary, such devices need only transmit to each other as necessary or desirable, and may actually refrain from exchanging data most of the time. For example, a machine in communication with or coupled with another machine via the Internet may not transmit data to the other machine for long period of time (e.g. weeks at a time). In addition, devices that are in communication with or coupled with each other may communicate directly or indirectly through one or more intermediaries.

Configured To: various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits. Various components may be described as performing a task or tasks, for convenience in the description. Such descriptions should be interpreted as including the phrase "configured to." Reciting a component that is configured to perform one or more tasks is expressly intended not to invoke 35 U.S.C. § 112(f) interpretation for that component.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

Means Plus Function Language: to aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

Ranges: it should be noted that the recitation of ranges of values in this disclosure are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the claims.

The invention claimed is:

1. A communication device system having an indoor unit and an outdoor unit located on both sides of a barrier comprising:
   the indoor unit comprising:
      an indoor unit downlink path having an indoor unit low noise amplifier in an on state;
      an indoor unit, uplink path receiving antenna in an indoor unit uplink path capable of receiving a first signal from a wireless user terminal at a first frequency and coupled to an indoor unit receive signal detector and amplifier (RSDA);
      an indoor unit controller capable of receiving an indication from the indoor unit RSDA that the first signal has been received and automatically turning on the indoor unit uplink path by activating indoor unit power amplifier and turning off the indoor unit downlink path by turning off the indoor unit low noise amplifier; and
      the indoor unit power amplifier capable of amplifying the first signal and sending the first signal to an indoor unit, uplink path transmitting antenna which is capable of transmitting the first signal at the first frequency to the outdoor unit;
   the outdoor unit comprising:
      an outdoor unit downlink path having an outdoor unit low noise amplifier in an on state;
      an outdoor unit, uplink path receiving antenna in an outdoor unit uplink path capable of receiving the first signal at the first frequency and coupled to an outdoor unit RSDA;
      an outdoor unit controller capable of receiving an indication from the outdoor unit RSDA that the first signal has been received and automatically turning on the outdoor unit uplink path by activating an outdoor unit power amplifier and turning off the outdoor unit downlink path by turning off the outdoor unit low noise amplifier; and
      the outdoor unit power amplifier capable of amplifying the first signal and sending the first signal to an outdoor unit, uplink path transmitting antenna which is capable of transmitting the first signal at the first frequency to a base station.

2. The system of claim 1, further comprising:
   an indoor unit, downlink path receiving antenna capable of receiving a second signal at a second frequency and coupled to the indoor unit low noise amplifier;
   the indoor unit low noise amplifier capable of amplifying the second signal and forwarding the second signal to an indoor unit, downlink path transmitting antenna which is capable of transmitting the second signal at the second frequency to a wireless user terminal.

3. The system of claim 2, further comprising:
   an outdoor unit, downlink path receiving antenna capable of receiving signals of a second frequency from the base station; and
   wherein the indoor unit, uplink path receiving antenna; outdoor unit, uplink path transmitting antenna; outdoor unit, downlink path receiving antenna; and indoor unit, downlink path receiving antenna are antenna arrays.

4. The system of claim 2 wherein the first signal is an analog signal and the second signal is an analog signal.

5. The system of claim 1, wherein the indoor unit power amplifier and indoor unit low noise amplifier cannot both be operating at the same time.

6. The system of claim 1, wherein the first frequency is in a range of about 2 GigaHertz (GHz) to 100 GHz.

7. The system of claim 1, wherein the indoor unit, uplink path receiving antenna and indoor unit, downlink path transmitting antenna are antenna arrays capable of RF beam steering.

8. The system of claim 1, wherein directions of the indoor unit, downlink path transmitting antenna and outdoor unit, uplink path transmitting antenna are each capable of being adjusted by RF beam steering.

9. A communication device comprising:
   a housing having a downlink path including a low noise amplifier in an on state when there is no uplink signal;
   a first antenna in an uplink path capable of receiving the uplink signal at a first frequency and coupled to a receive signal detector and amplifier (RSDA);
   a controller capable of receiving an indication from the RSDA that the uplink signal has been received and automatically turning on the uplink path by activating a power amplifier and turning off the downlink path by turning off the low noise amplifier, and wherein the controller does not allow the power amplifier and low noise amplifier to both be operating at the same time; and
   the power amplifier capable of amplifying the uplink signal and sending the uplink signal to a second antenna which is capable of transmitting the uplink signal at the first frequency.

10. The communication device of claim 9, further comprising:
   a phase shifter in the uplink path controlled by the controller to direct the beam of the uplink signal.

11. A communication system having a first unit and a second unit located on both sides of a barrier comprising:
   the first unit comprising:
      a first unit downlink path having a first unit low noise amplifier in an on state;
      a first unit receiving antenna in a first uplink path capable of receiving a first signal at a first frequency and coupled to a first unit receive signal detector and amplifier (RSDA);
      a first unit controller capable of receiving an indication from the first unit RSDA that the first signal has been received and automatically turning on the first uplink path by activating a first unit power amplifier and turning off the first unit downlink path by turning off the first unit low noise amplifier, wherein the first unit controller does not allow the first unit power amplifier and the first unit low noise amplifier to both be operating at the same time; and
      the first unit power amplifier capable of amplifying the first signal and sending the first signal to a first unit transmitting antenna which is capable of transmitting the first signal at the first frequency to the second unit; and the second unit comprising:
- a second unit downlink path having a second unit low noise amplifier in an on state;
- a second unit receiving antenna in a second unit uplink path capable of receiving the first signal at the first frequency and coupled to a second unit receive signal detector and amplifier (RSDA);
- a second unit controller capable of receiving an indication from the second unit RSDA that the first signal has been received and automatically turning on the second unit uplink path by activating a second unit power amplifier and turning off the second unit downlink path by turning off the second unit low noise amplifier;
- wherein the second unit controller operates a second unit phase shifter to direct the alignment of the first signal; and
- the second unit power amplifier capable of amplifying the first signal and sending the first signal to a second unit transmitting antenna which is capable of transmitting the first signal at the first frequency to a base station.

12. The system of claim 11, wherein the first signal frequency is in a range of approximately 2 GigaHertz (GHz) to approximately 100 GHz.

13. The system of claim 11, wherein the second unit transmitting antenna is an antenna array capable of RF beam steering.

14. The system of claim 11, wherein the second unit transmitting antenna is an antenna array.

15. The system of claim 11, wherein a direction of the second unit transmitting antenna is capable of being adjusted by by RF beam steering.

* * * * *